(12) United States Patent
Groeper et al.

(10) Patent No.: US 10,131,660 B2
(45) Date of Patent: Nov. 20, 2018

(54) TETRAHYDRO-AZEPINOQUINOLINES AS AGONISTS OF THE 5-HT$_{2C}$ RECEPTOR

(71) Applicant: Sunnylife Pharma, Inc., Indianapolis, IN (US)

(72) Inventors: Jonathan A. Groeper, Greenwood, IN (US); Xibin Liao, Edison, NJ (US); Zhijian Lu, Plainfield, IN (US)

(73) Assignee: Sunnylife Pharma, Inc., Indianapolis, IN (US)

( * ) Notice: Subject to any disclaimer, the term of this patent is extended or adjusted under 35 U.S.C. 154(b) by 68 days.

(21) Appl. No.: 15/506,045

(22) PCT Filed: Aug. 26, 2015

(86) PCT No.: PCT/US2015/047017
§ 371 (c)(1),
(2) Date: Feb. 23, 2017

(87) PCT Pub. No.: WO2016/033228
PCT Pub. Date: Mar. 3, 2016

(65) Prior Publication Data
US 2018/0215752 A1      Aug. 2, 2018

Related U.S. Application Data

(60) Provisional application No. 62/043,046, filed on Aug. 28, 2014.

(51) Int. Cl.
| | | |
|---|---|---|
| C07D 471/04 | (2006.01) |
| A61P 3/04 | (2006.01) |
| A61P 13/10 | (2006.01) |
| A61P 25/18 | (2006.01) |
| A61P 25/24 | (2006.01) |
| A61P 3/10 | (2006.01) |

(52) U.S. Cl.
CPC .............. *C07D 471/04* (2013.01); *A61P 3/04* (2018.01); *A61P 3/10* (2018.01); *A61P 13/10* (2018.01); *A61P 25/18* (2018.01); *A61P 25/24* (2018.01)

(58) Field of Classification Search
None
See application file for complete search history.

(56) References Cited

U.S. PATENT DOCUMENTS

| | | |
|---|---|---|
| 3,987,047 A | 10/1976 | Griss et al. |
| 2007/0281918 A1 | 12/2007 | Araldi et al. |
| 2013/0143870 A1 | 6/2013 | Grauert et al. |

OTHER PUBLICATIONS

International Application No. PCT/US2015/047017; International Filing Date: Aug. 26, 2015. Notification of Transmittal of the International Search Report and The Written Opinion of the International Search Authority, or the Declaration, dated Nov. 27, 2015. (12 pages).
International Application No. PCT/US2015/047017; Search History. Date of Search: Oct. 16, 2015. (8 pages).
Hinschberger, Antoine et al. New Benzo[h] [1,6] naphthyridine and Azepino [3,2-c] quinoline Derivaties as Selective Antagonist of 5-HT4 Receptors: Binding Profile and Pharmacological Characterization. Received Jun. 7, 2002. 2003, American Chemical Society. Journal of Medicinal Chemistry, 2003, vol. 46, No. 1. Published Dec. 7, 2002. (10 pages).

*Primary Examiner* — Samantha L Shterengarts
(74) *Attorney, Agent, or Firm* — White and Williams LLP

(57) ABSTRACT

Certain tetrahydro-azepinoquinolines of structural formula I are agonists of the mammalian 5-HT$_{2c}$ receptor, and, in particular, are selective agonists of the mammalian 5-HT$_{2c}$ receptor. The compounds of the present invention are therefore useful for the treatment, control, or prevention of diseases, conditions, or disorders responsive to stimulation of the 5-HT$_{2c}$ receptor, such as obesity, obesity-related conditions, and certain CNS-related disorders, including schizophrenia and depression. They are also useful as aids for tobacco smoking cessation.

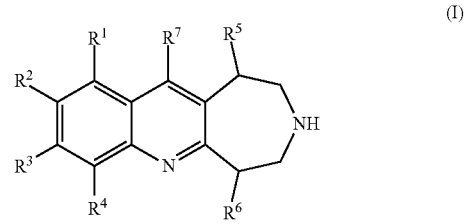

(I)

19 Claims, No Drawings

TETRAHYDRO-AZEPINOQUINOLINES AS AGONISTS OF THE 5-HT$_{2C}$ RECEPTOR

CROSS REFERENCE TO RELATED APPLICATIONS

This application is the National Stage of International Application No. PCT/US2015/047017, filed Aug. 26, 2015, which claims priority from U.S. Provisional Application 62/043,046, filed Aug. 28, 2014. The entire contents of the priority application are hereby incorporated by reference as if fully set forth herein.

FIELD OF THE INVENTION

The present invention relates to novel tetrahydro-azepinoquinolines, their synthesis, and their use as agonists of the 5-HT$_{2C}$ receptor to decrease food intake, induce satiety, or otherwise control weight gain as well as their use to aid in tobacco smoking cessation. More particularly, the compounds of the present invention are selective agonists of the 5-HT$_{2C}$ receptor and are thereby useful for the treatment of conditions and disorders responsive to selective stimulation of the 5-HT$_{2C}$ receptor, such as obesity, obesity-related conditions, and certain CNS-related disorders. The compounds of the present invention also have a treatment effect for tobacco smoking cessation.

BACKGROUND OF THE INVENTION

Obesity is a life-threatening disorder where there is increased risk of morbidity and mortality, particularly from associated diseases such as hypertension, diabetes mellitus, ischemia, dyslipidemia, coronary heart disease, cancer and gall bladder disease. The economic consequences significantly impact the U.S. health care system, both through direct and indirect (costs associated with morbidity and mortality) medical costs. In 2008 dollars, the costs of medical care of obesity were roughly $147 billion (Finkelstein et al., Health Affairs 2009; 28: w822-2831). Complications from these diseases lead to a decrease in quality of life, excessive burden on health care resources and even death.

Obesity is defined as having a body mass index (BMI) of ≥30 kg/m$^2$ and is calculated as follows: BMI=(mass in kg)÷(height in meters)$^2$. An individual with a BMI between 25 and 29.9 is considered overweight and may also be at risk for the associated diseases and their complications as stated above. There are other measures that are indicative of obesity such as waist circumference, waist-to-height ratio or waist-to-hip ratio (Heitmann, B L, Lissner, L Obesity Reviews. 2011; 12:478-81). Obesity may also be defined based on body fat content which would be >25% for males and >30% for females. Nonetheless, BMI generally has been shown to correlate with morbidity and mortality. As BMI increases there is an increased risk of death from causes that are independent of other risk factors (Flegal, K M, et al. JAMA. 2013; 71:71-82). Research has shown that a modest reduction in BMI can significantly reduce the risk of developing coronary heart disease. The most common diseases associated with obesity are cardiovascular disease, diabetes mellitus, gall bladder disease, and diseases of the reproductive organs.

Consideration of treating a patient for weight loss is not only for the reason of decreasing morbidity and mortality, but also because there is strong data from randomized control trials that weight loss reduces risk factors for additional diseases. Thus, treatment of the overweight and obese conditions will reduce the risk and the consequence of other diseases. The most common diseases associated with obesity are coronary heart disease, diabetes mellitus, cancers (most notably endometrial, breast, and colon), hypertension, dyslipidemia, stroke, liver and gall bladder disease, sleep apnea and respiratory problems, osteoarthritis and diseases of the reproductive organs. Research has shown that a modest reduction in BMI can significantly reduce the risk of developing most of these diseases (Clinical Guidelines on the Identification, Evaluation and Treatment of Overweight and Obesity in Adults: The Evidence Report. NIH Publication No. 98-4083).

Obesity is a growing health care concern in the Western hemisphere and increasingly worldwide. Major countries with rapidly increasing obese populations include the United States, Mexico, India and China. The increased number of obese children and adults is due largely to the increasing availability of and preference for high fat foods. Another important factor has been decreased activity in the daily routine of many people. From 1994 to 2010 there has been an increase in the incidence of obesity in the USA of over 60% such that 35.7% of adults and 17% of children in the United States are now considered obese. From 2002 to 2010, the number of individual states in the USA with obese (BMI≥30) populations of 25% or greater has risen from three to thirty-six (Ogden C L, et al. NCHS data brief, no 82. Hyattsville, Md.: National Center for Health Statistics, 2012).

Despite the magnitude of the problem and the corresponding toll on quality of life and health care costs, there are only limited drug-treatment options currently available (Withrow, D, Alter, D A Obesity Reviews. 2011; 12:131-41). Typically, the first line of treatment a doctor may advise to a patient is a modified diet and lifestyle changes such as reducing overall caloric intake, especially from fats, and increasing physical activity. Unfortunately, many patients find maintaining an adequate level of diet and exercise to be difficult and require additional help from drug therapy to achieve their weight loss recommendation.

Marketed drugs currently available have not been overly successful as treatments for obesity due to either poor efficacy or poorly tolerated side-effect profiles. One of the more efficacious drugs was dexfenfluramine (Redux™) which acted indirectly on the 5-hydroxytryptamine (5-HT) pathway, but reports of cardiac valve defects in up to one third of patients led to its withdrawal by the FDA in 1998. The N-dealkylated metabolite norfenfluramine is a potent agonist of 5-HT$_{2B}$ which is thought to be responsible for the cardiac valve effects (Fitzgerald L W, et al. Mol Pharmacol 2000; 57(1):75-81). Other drugs have been launched in the USA or Europe: orlistat (Xenical™), a drug that prevents absorption of fat by the inhibition of pancreatic lipase, sibutramine (Reductil™), a 5-HT/noradrenaline re-uptake inhibitor and rimonobant (Accomplia™). However, side effects associated with these products have limited their long-term utility. Xenical™ is reported to cause gastrointestinal distress in patients, while rimonobant and sibutramine were removed from the market in 2009 and 2010, respectively, due to intolerable side effects.

Serotonin (5-hydroxytryptamine, 5-HT) mediates a wide range of physiological responses through its seven subfamilies (5-HT$_1$-5-HT$_7$) and at least fourteen receptors (Barnes N M, Sharp T, Neuropharmacology. 1999; 38(8):1083-152; Hoyer D, et al. Pharmacol Biochem Behav. 2002; 71(4): 533-54; Kroeze W K, et al. Curr Top Med Chem. 2002; 2(6):507-28). Serotonin receptor modulators have been targeted as therapeutic agents for many years and several marketed drugs target serotonin receptor activities. For example, buspirone used to treat anxiety and depression is a selective 5-HT$_{1A}$ receptor partial agonist; sumatriptan used to treat migraine is a selective 5-HT$_{1B}$ and 5-HT$_{1D}$ receptor agonist and several typical and atypical antipsychotic drugs have inverse agonist activity at 5-HT$_{2A}$ and 5-HT$_{2C}$ receptors (Meltzer H Y, Roth B L. J Clin Invest. 2013 Dec. 2; 123(12):4986-91). In 2012, the FDA approved the use of lorcaserin, a 5-HT$_{2C}$ receptor agonist for the treatment of obesity (Thomsen W J, et al. J Pharmacol Exp Ther. 2008; 325(2):577-87; Martin C K, et al. J Clin Endocrinol Metab. 2011; 96(3):837-45: Smith S R, et al. Obesity (Silver Spring). 2009; 17(3):494-503). Modulation of serotonin receptors has application in abroad range of therapeutic areas.

The 5-HT$_2$ receptor subfamily consists of 5-HT$_{2A}$, 5-HT$_{2B}$, and 5-HT$_{2C}$ receptors. They share high homology in their amino acid sequences, couple to the G$_q$ family of G-proteins, and activate phospholipase C (PLC). Activation of 5-HT$_2$ receptors leads to increases in intracellular levels of Ca$^{2+}$ and phosphoinositol hydrolysis. The 5-HT$_{2C}$ receptor is predominantly expressed in the choroid plexus, cortex, basal ganglia, hippocampus and hypothalamus and has been implicated in appetite regulation, anxiety, depression, schizophrenia, and neuroendocrine regulation (Bickerdike M J. Curr Top Med Chem. 2003; 3(8):885-97; Leysen J E. Curr Drug Targets CNS Neurol Disord. 2004; 3(1):11-26; Serrstti A, et al. Expert Opin Ther Targets. 2004; 8(1):15-23; Higgins G A, et al. Trends Pharmacol Sci. 2013; 34(10): 560-70; Wacker D A, Miller K J. Curr Opin Drug Discov Devel. 2008; 11 (4):438-45). In the last ten years, there have been many medicinal chemistry efforts to discover potent and selective 5-HT$_{2C}$ receptor agonists to treat obesity, schizophrenia, and mood disorders [Huck B R, et al. Bioorg Med Chem Lett. 2006; 16(15):4130-4; Huck B R, et al. Bioorg Med Chem Lett. 2006; 16(11):2891-4; Siuciak J A, et al Neuropharmacology. 2007 February; 52(2):279-90; Grauer S M, et al. Psychopharmacology (Berl). 2009 May; 204(1):37-48; Marquis K L, et al. J Pharmacol Exp Ther. 2007 January; 320(1):486-96; Liu K K, et al. Bioorg Med Chem Lett 2010; 20(1):266-71]; Dunlop J. et al. J Pharmacol Exp Ther. 2011 June; 337(3):673-80); Miller K J, Molecular Interventions 2005; 5(5): 282-291. Several compounds have been advanced to human clinical trials, including vabicaserin for schizophrenia, a compound from a company Athersys, ATHX-105, for obesity, and lorcaserin for obesity. Lorcaserin is currently the only 5-HT$_{2C}$ receptor agonist approved by the FDA for the treatment of obesity.

One of the challenges to discover novel selective 5-HT$_{2C}$ receptor agonists is achieving selectivity against 5-HT$_{2A}$ and 5-HT$_{2B}$ receptors due to their high similarities in molecular structure, pharmacology and signaling pathways. The 5-HT$_{2A}$ receptor is widely expressed in the central nervous system (CNS) and peripheral tissues. Activation of the 5-HT$_{2A}$ receptor can result in hallucination (Nichols D E. Pharmacol Ther. 2004; 101 (2):131-81), platelet aggregation, and vascular smooth muscle contraction. The 5-HT$_{2B}$ receptor is expressed in the liver, kidney, lung, heart, pancreas, spleen, brain, spinal cord, gastrointestinal tract, placenta, and coronary and pulmonary arteries. Activation of 5-HT$_{2B}$ receptors has been linked to valvulopathy (Fitzgerald L W, et al. Mol Pharmacol. 2000; 57(1):75-81). Therefore, high selectivity against the 5-HT$_{2C}$ receptor and the 5-HT$_{2B}$ receptor is necessary to minimize the potential side effects of a 5-HT$_{2C}$ receptor agonist especially in the treatment of obesity and other chronic conditions and diseases.

The clinical dose of lorcaserin is limited by sub-optimal selectivity over the 5-HT$_{2A}$ receptor. This resulted in unacceptable CNS effects at the higher doses of lorcaserin evaluated in clinical trials. More selective agonists, such as those of the present invention, would be able to achieve greater efficacy of 5-HT$_{2C}$-mediated diseases through more effective agonism of the 5-HT$_{2C}$ receptor at higher doses that do not agonize the 5-HT$_{2A}$ receptor. In addition to feeding behavior, it is believed that 5-HT$_{2C}$ may play a role in obsessive compulsive disorder, some forms of depression, and epilepsy. Accordingly, 5-HT$_{2C}$ agonists can have antipanic properties as well as properties useful for the treatment of sexual dysfunction. The potential of 5-HT$_{2C}$ agonists to treat substance abuse is discussed in "From obesity to substance abuse: therapeutic opportunities for 5-HT$_{2C}$ receptor agonists," Trends in Pharmacol Sci., 2013; 34: 560-570. For example, lorcaserin has been reported to decrease nicotine self-administration in female rats [Levin, E D, et al, J. Pharmacol. Exp. Ther., 338(3), 890-896 (2011)] and in a press release dated Nov. 3, 2014, Eisai and Arena Pharmaceuticals reported results of a Phase 2 trial in humans suggesting that the compound may be useful to aid in tobacco smoking cessation.

In summary, the 5-HT$_{2C}$ receptor is a validated and well-accepted receptor target for the treatment of metabolic and CNS-related disorders, and it can be seen that there is a need in the medical arts for selective 5-HT$_{2C}$ agonists which safely decrease food intake and body weight. The present invention is directed to such compounds which are useful to treat obesity as well as other diseases directly or indirectly associated with 5-HT$_{2C}$ system dysfunction, such as Type 2 diabetes, dyslipidemia, depression, schizophrenia, obsessive-compulsive disorder, drug abuse, sleep disorders, anxiety, epilepsy, tobacco smoking and the maladies that may arise from these diseases. Importantly, the compounds of the present invention are potent 5-HT$_{2c}$ agonists that possess superior selectivity against 5-HT$_{2A}$ and 5-HT$_{2B}$ whose activation has limited the utility of previous 5-HT$_{2C}$ agonists.

U.S. Pat. No. 3,987,047 (Boehringer Ingelheim) discloses tetrahydro-azepinoquinolines with utility as anorectic agents. International patent publications WO 2003/086306 (Arena); WO 2005/000849; WO 2005/003096 (Arena); WO 2006/004931 (Athersys); WO 2006/028961 (Athersys); WO 2006/071740 (Arena); WO 2006/077025 (Roche); WO 2006/117304 (Roche); WO 2007/016029 (Wyeth); WO 2007/030150 (Wyeth); WO 2007/047671 (Wyeth); WO 2007/081299 (Athersys); WO 2007/084622 (Athersys); WO 2007/140213 (Forest); WO 2008/117169 (Pfizer); WO 2008/009125 (Sun Guangri); WO 2010/060952 (Boehringer Ingelheim); WO 2011/111817 (Astellas); as well as U.S. Pat. Nos. 7,514,422; 7,547,699; 7,718,647; 7,893,051; 7,928, 099; 7,981,896; 7,981,919; 8,153,621; and 8,232,311 disclose 5-HT$_{2C}$ modulators or compounds that affect food intake. Lorcaserin (Arena) is disclosed in WO 2003/086306 and U.S. Pat. Nos. 6,953,787; 7,514,422; 7,977,329; 8,168, 624; and 8,367,657. However, none of the above issued patents or published patent applications discloses the compounds of the present invention.

It is therefore an object of the present invention to provide novel fused tetrahydroazepine compounds which are 5-HT$_{2C}$ receptor agonists and thereby useful to treat obesity, obesity-related disorders, certain psychiatric conditions, and as an aid to tobacco smoking cessation. It is another object of the present invention to provide novel fused tetrahydroazepine compounds which are selective 5-HT$_{2C}$ receptor agonists relative to the 5-HT$_{2A}$ and 5-HT$_{2B}$ receptors. It is another object of the present invention to provide pharmaceutical compositions comprising the 5-HT$_{2C}$ receptor agonists or ligands of the present invention with a pharmaceutically acceptable carrier.

It is another object of the present invention to provide methods for the treatment or prevention of obesity, obesity-related conditions, and certain psychiatric disorders by administering the compounds and pharmaceutical compositions of the present invention to a mammal in need thereof.

It is another object of the present invention to provide methods for aiding tobacco smoking cessation by administering the compounds and pharmaceutical compositions of the present invention to a mammal in need thereof.

It is another object of the present invention to provide methods for the treatment or prevention of disorders, diseases, or conditions responsive to the activation of the 5-HT$_{2C}$ receptor in a mammal in need thereof by administering the compounds and pharmaceutical compositions of the present invention.

SUMMARY OF THE INVENTION

The present invention relates to novel tetrahydro-azepinoquinolines of structural formula I:

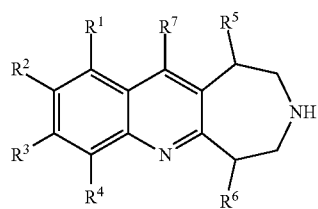

The compounds of structural formula I are effective as agonists of the 5-HT$_{2C}$ receptor and are particularly effective as selective agonists of the 5-HT$_{2C}$ receptor. They are therefore useful for the treatment, control, or prevention of disorders and conditions responsive to selective activation of the 5-HT$_{2C}$ receptor, such as obesity, obesity-related disorders, such as Type 2 diabetes, insulin resistance, dyslipidemia, atherosclerosis, and Metabolic Syndrome, and certain CNS-related disorders, including schizophrenia, depression, psychosis, urinary incontinence, and epilepsy.

The compounds of the present invention also have a treatment effect for tobacco smoking cessation and may therefore be useful as aids for tobacco smoking cessation.

The present invention also relates to pharmaceutical compositions comprising the compounds of the present invention and a pharmaceutically acceptable carrier.

The present invention also relates to methods for the treatment, control, or prevention of disorders, diseases, or conditions responsive to the selective modulation of the 5-HT$_{2C}$ receptor in a mammal in need thereof by administering the compounds and pharmaceutical compositions of the present invention.

The present invention also relates to methods for the treatment or control of obesity and obesity-related disorders, such as Type 2 diabetes, insulin resistance, dyslipidemia, atherosclerosis, and Metabolic Syndrome, by administering the compounds and pharmaceutical compositions of the present invention.

The present invention also relates to methods for the treatment or control of psychiatric conditions, such as schizophrenia, depression, psychosis, and urinary incontinence, by administering the compounds and pharmaceutical compositions of the present invention.

The present invention also relates to methods for aiding tobacco smoking cessation by administering the compounds and pharmaceutical compositions of the present invention.

The present invention also relates to methods for the treatment or control of obesity and obesity-related disorders, such as Type 2 diabetes, insulin resistance, dyslipidemia, atherosclerosis, and Metabolic Syndrome, by administering the compounds of the present invention in combination with a therapeutically effective amount of another agent known to be useful to treat these conditions.

The present invention also relates to methods for aiding tobacco smoking cessation by administering the compounds and pharmaceutical compositions of the present invention in combination with a therapeutically effective amount of another agent known to have a treatment effect for tobacco smoking cessation.

The present invention also relates to methods for the treatment or control of obesity by administering the compounds of the present invention in combination with a therapeutically effective amount of another agent known to be useful to treat this condition.

The present invention further relates to the use of the compounds of the present invention in the preparation of a medicament useful for the treatment, control, or prevention of diseases, disorders, or conditions responsive to the selective modulation of the 5-HT$_{2C}$ receptor in a mammal in need thereof by administering the compounds and pharmaceutical compositions of the present invention.

DETAILED DESCRIPTION OF THE INVENTION

The present invention is concerned with tetrahydro-azepinoquinolines useful as agonists of the 5-HT$_{2C}$ receptor, in particular, as selective agonists of the 5-HT$_{2C}$ receptor. Compounds of the present invention are described by structural formula I:

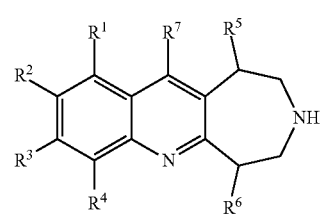

and pharmaceutically acceptable salts thereof; wherein
R$^1$ is selected from the group consisting of:
  hydrogen,
  halogen,
  C$_{2-6}$ alkyl, optionally substituted with one to five substituents independently selected from fluorine and hydroxy,
  (CH$_2$)$_m$—C$_{3-7}$ cycloalkyl,
  C$_{2-6}$ alkoxy, optionally substituted with one to five substituents independently selected from fluorine and hydroxy,
  C$_{3-7}$ cycloalkyl oxy,
  C$_{1-6}$ alkylthio, optionally substituted with one to five substituents independently selected from fluorine and hydroxy, $C_{1-6}$ alkylsulfonyl, optionally substituted with one to five substituents independently-selected from fluorine and hydroxy,
—O(CH$_2$)$_n$-aryl, and
—O(CH$_2$)$_n$-heteroaryl;
wherein cycloalkyl and cycloalkyloxy are optionally substituted with 1 to 3 groups independently selected from halogen, hydroxyl, cyano, CO$_2$H, $C_{1-4}$ alkyloxycarbonyl, $C_{1-4}$ alkyl, and $C_{1-4}$ alkoxy, wherein alkyl and alkoxy are optionally substituted with one to five fluorines; wherein aryl and heteroaryl are optionally substituted with 1 to 5 groups independently selected from halogen, hydroxyl, cyano, CO$_2$H, $C_{1-4}$ alkyloxycarbonyl, $C_{1-4}$ alkyl, and $C_{1-4}$ alkoxy, wherein alkyl and alkoxy are optionally substituted with one to five fluorines; and (CH$_2$)$_m$ or (CH$_2$)$_n$ is optionally substituted with 1 to 2 substituents independently selected from fluorine, hydroxyl, methyl, trifluoromethyl, and methoxy, or wherein two substituents when on the same methylene (CH$_2$) group are taken together with the carbon atom to which they are attached to form a cyclopropyl group;
R$^2$ is selected from the group consisting of:
hydrogen,
halogen,
$C_{1-4}$ alkyl, and
$C_{3-6}$ cycloalkyl;
R$^3$ is hydrogen or halogen;
R$^4$ is selected from the group consisting of:
halogen,
$C_{2-6}$ alkyl, optionally substituted with one to five substituents independently selected from fluorine and hydroxy,
$C_{3-7}$ cycloalkyl,
$C_{2-6}$ alkoxy, optionally substituted with one to five substituents independently selected from fluorine and hydroxy, and
$C_{3-7}$ cycloalkyloxy;
wherein cycloalkyl and cycloalkyloxy are optionally substituted with 1 to 3 groups independently selected from halogen, hydroxyl, cyano, CO$_2$H, $C_{1-4}$ alkyloxycarbonyl, $C_{1-4}$ alkyl, and $C_{1-4}$ alkoxy, wherein alkyl and alkoxy are optionally substituted with one to five fluorines;
R$^5$ and R$^6$ are each independently hydrogen or methyl;
R$^7$ is selected from the group consisting of:
hydrogen,
halogen,
$C_{1-3}$ alkyl, optionally substituted with, one to five substituents independently selected from fluorine and hydroxy,
$C_{1-3}$ alkoxy, optionally substituted with one to five substituents independently selected from fluorine and hydroxy,
$C_{1-3}$ alkylthio, optionally substituted with one to five substituents independently selected from fluorine and hydroxy,
$C_{1-3}$ alkylsulfonyl, optionally substituted with one to five substituents independently selected from fluorine and hydroxyl,
amino,
$C_{1-4}$ alkylamino, and
di-($C_{1-4}$ alkyl)amino;
m is an integer from 0 to 1; and
n is an integer from 0 to 2;
with the proviso that when R$^1$ is hydrogen or halogen and R$^2$ is hydrogen, halogen or methyl, then R$^4$ cannot be halogen.

In one embodiment of the compounds of the present invention, R$^1$ is halogen; R$^2$ is hydrogen or halogen; R$^3$ is hydrogen or halogen; R$^4$ is optionally substituted $C_{3-6}$ cycloalkyl; R$^5$ and R$^6$ are both hydrogen; and R$^7$ is hydrogen or methyl. In a class of this first embodiment, R$^4$ is cyclopropyl. In another class of this first embodiment, R$^1$ is fluorine or chlorine; R$^2$ is hydrogen, fluorine, or chlorine; R$^3$ is hydrogen or fluorine; R$^4$ is optionally substituted $C_{3-6}$ cycloalkyl; and R$^7$ is hydrogen or methyl. In a subclass of this class, R$^4$ is cyclopropyl.

In a second embodiment of the compounds of the present invention, R$^1$ is halogen; R$^2$ is hydrogen or halogen; R$^3$ is hydrogen or halogen; R$^4$ is optionally substituted $C_{3-6}$ cycloalkyloxy; R$^5$ and R$^6$ are both hydrogen; and R$^7$ is hydrogen or methyl. In a class of this first embodiment, R$^4$ is optionally substituted cyclohexyloxy or cycloheptyloxy. In another class of this first embodiment, R$^1$ is fluorine or chlorine; R$^2$ is hydrogen, fluorine, or chlorine; R$^3$ is hydrogen or fluorine; R$^4$ is optionally substituted $C_{3-6}$ cycloalkyloxy; and R$^7$ is hydrogen or methyl. In a subclass of this class, R$^4$ is optionally substituted cyclohexyloxy or cycloheptyloxy.

In a third embodiment of the compounds of the present invention, R$^1$ is selected from the group consisting of:
$C_{5-7}$ cycloalkyloxy, optionally substituted optionally substituted with 1 to 3 groups independently selected from halogen, hydroxyl, cyano, CO$_2$H, $C_{1-4}$ alkyloxycarbonyl, $C_{1-4}$ alkyl, and $C_{1-4}$ alkoxy; and
phenoxy, optionally substituted with 1 to 3 groups independently selected from halogen, hydroxyl, cyano, $C_{1-4}$ alkyloxycarbonyl, $C_{1-4}$ alkyl, and $C_{1-4}$ alkoxy;
R$^2$ and R$^3$ are each hydrogen or halogen;
R$^4$ is halogen;
R$^5$ and R$^6$ are both hydrogen; and
R$^7$ is hydrogen or methyl.
In a class of this third embodiment, R$^2$ is hydrogen, fluorine, or chlorine; R$^3$ is hydrogen or fluorine; R$^4$ is chlorine or fluorine; and R$^7$ is hydrogen or methyl. In a subclass of this class, R$^1$ is optionally substituted cyclohexyloxy or cycloheptyloxy. In another subclass of this class, R$^1$ is phenoxy wherein phenoxy is optionally substituted with 1 to 3 groups independently selected from halogen, hydroxyl, cyano, $C_{1-4}$ alkyloxycarbonyl, $C_{1-4}$ alkyl, and $C_{1-4}$ alkoxy.

In fourth embodiment of the compounds of the present invention, R$^5$ and R$^6$ are both hydrogen.

In a fifth embodiment of the present invention are the following specific compounds of structural formula (I):
10-chloro-1-cyclopropyl-2,3,4,5-tetrahydro-1H-azepino[4,5-b]quinoline;
7-cyclopropyl-8,10-difluoro-11-methyl-2,3,4,5-tetrahydro-1H-azepino[4,5-b]quinoline;
7-ethyl-10-fluoro-2,3,4,5-tetrahydro-1H-azepino[4,5-b]quinoline;
7-ethyl-2,3,4,5-tetrahydro-1H-azepino[4,5-b]quinoline;
7-cyclopropyl-10-fluoro-2,3,4,5-tetrahydro-1H-azepino[4,5-b]quinoline;
7-chloro-10-ethyl-9-fluoro-2,3,4,5-tetrahydro-1H-azepino[4,5-b]quinoline;
7-chloro-10-ethyl-2,3,4,5-tetrahydro-1H-azepino[4,5-b]quinoline;
7-cyclopropyl-8,10-difluoro-2,3,4,5-tetrahydro-1H-azepino[4,5-b]quinoline;
10-ethyl-7,9-difluoro-2,3,4,5-tetrahydro-1H-azepino[4,5-b]quinoline;
7-chloro-10-cyclohexyloxy-11-methyl-2,3,4,5-tetrahydro-1H-azepino[4,5-b]quinoline;
7-cyclopropyl-8,10-difluoro-2,3,4,5-tetrahydro-1H-azepino[4,5-b]quinoline;
7-isopropyl-2,3,4,5-tetrahydro-1H-azepino[4,5-b]quinoline;

10-ethyl-7-fluoro-2,3,4,5-tetrahydro-1H-azepino[4,5-b]quinoline;
10-chloro-7-ethyl-2,3,4,5-tetrahydro-1H-azepino[4,5-b]quinoline;
7-cyclopropl-9,10-difluoro-2,3,4,5-tetrahydro-1H-azepino[4,5-b]quinoline;
7-cyclopropyl-9,10-difluoro-11-methyl-2,3,4,5-tetrahydro-1H-azepino[4,5-b]quinoline;
10-chloro-7-cyclopropyl-9-flour-2,3,4,5-tetrahydro-1H-azepino[4,5-b]quinoline;
7-fluoro-10-isopropyl-2,3,4,5-tetrahydro-1H-azepino[4,5-b]quinoline;
7-chloro-10-(3-fluorophenoxy)-2,3,4,5-tetrahydro-1H-azepino[4,5-b]quinoline;
7-cycloheptyloxy-10-fluoro-11-methyl-2,3,4,5-tetrahydro-1H-azepino[4,5-b]quinoline;
7-cyclohexyloxy-10-fluoro-11-methyl-2,3,4,5-tetrahydro-1H-azepino[4,5-b]quinoline;
7-cyclopropyl-10-ethyl-9-fluoro-2,3,4,5-tetrahydro-1H-azepino[4,5-b]quinoline;
10-chloro-7-cyclopropyl-11-methyl-2,3,4,5-tetrahydro-1H-azepino[4,5-b]quinoline;
10-cyclopropyl-7-fluoro-2,3,4,5-tetrahydro-1H-azepino[4,5-b]quinoline;
7-chloro-10-phenoxy-2,3,4,5-tetrahydro-1H-azepino[4,5-b]quinoline;
7-cyclopropyl-9-fluoro-10-methyl-2,3,4,5-tetrahydro-1H-azepino[4,5-b]quinoline;
7-cyclohexyloxy-10-fluoro-2,3,4,5-tetrahydro-1H-azepino[4,5-b]quinoline;
7-chloro-10-isopropoxy-11-methyl-2,3,4,5-tetrahydro-1H-azepino[4,5-b]quinoline;
7-chloro-10-cyclohexyloxy-2,3,4,5-tetrahydro-1H-azepino[4,5-b]quinoline;
7-chloro-10-clolopentyloxy-9-fluoro-2,3,4,5-tetrahydro-1H-azepino[4,5-b]quinoline;
7-chloro-10-cyclopentyloxy-2,3,4,5-tetrahydro-1H-azepino[4,5-b]quinoline;
7-chloro-10-cycloheptyloxy-11-methyl-2,3,4,5-tetrahydro-1H-azepino[4,5-b]quinoline;
7-chloro-9-cyclopropyl-2,3,4,5-tetrahydro-1H-azepino[4,5-b]quinoline;
7-chloro-10-cycloheptyloxy-2,3,4,5-tetrahydro-1H-azepino[4,5-b]quinoline;
7-chloro-10-cyclohexyloxy-11-ethyl-2,3,4,5-tetrahydro-1H-azepino[4,5-b]quinoline;
7-chloro-10-(3-fluorophenoxy)-2,3,4,5-tetrahydro-1H-azepino[4,5-b]quinoline;
10-benzyloxy-7-chloro-2,3,4,5-tetrahydro-1H-azepino[4,5-b]quinoline;
10-cyclopentyloxy-7-ethyl-9-fluoro-2,3,4,5-tetrahydro-1H-azepino[4,5-b]quinoline;
10-cyclopentyloxy-7-cyclopropyl-2,3,4,5-tetrahydro-1H-azepino[4,5-b]quinoline;
7-chloro-10-(2-fluorophenoxy)-11-methyl-2,3,4,5-tetrahydro-1H-azepino[4,5-b]quinoline;
10-cyclohexyloxy-7-fluoro-2,3,4,5-tetrahydro-1H-azepino[4,5-b]quinoline;
10-chloro-9-methoxy-7-cyclopropyl-2,3,4,5-tetrahydro-1H-azepino[4,5-b]quinoline;
7-chloro-10-cyclohexyloxy-11-dimethylamino-2,3,4,5-tetrahydro-1H-azepino[4,5-b]quinoline;
7-chloro-10-cyclobutyloxy-2,3,4,5-tetrahydro-1H-azepino[4,5-b]quinoline;
7,9-diisopropyl-2,3,4,5-tetrahydro-1H-azepino[4,5-b]quinoline; and
10-cyclopentyloxy-7-ethyl-2,3,4,5-tetrahydro-1H-azepino[4,5-b]quinoline;
and pharmaceutically acceptable salts thereof.

In a class of this fifth embodiment are the following specific compounds of structural formula (I):
10-chloro-7-cyclopropyl-2,3,4,5-tetrahydro-1H-azepino[4,5-b]quinoline;
7-cyclopropyl-8,10-difluoro-11-methyl-2,3,4,5-tetrahydro-1H-azepino[4,5-b]quinoline;
7-cyclopropyl-8,10-difluoro-2,3,4,5-tetrahydro-1H-azepino[4,5-b]quinoline;
7-chloro-10-cyclohexyloxy-11-methyl-2,3,4,5-tetrahydro-1H-azepino[4,5-b]quinoline;
7-cyclopropyl-9,10-difluoro-2,3,4,5-tetrahydro-1H-azepino[4,5-b]quinoline;
7-cyclopropyl-9,10-difluoro-11-methyl-2,3,4,5-tetrahydro-1H-azepino[4,5-b]quinoline;
10-chloro-7-cyclopropyl-9-fluoro-2,3,4,5-tetrahydro-1H-azepino[4,5-b]quinoline;
7-chloro-10-(3-fluorophenoxy)-2,3,4,5-tetrahydro-1H-azepino[4,5-b]quinoline;
7-cycloheptyloxy-10-fluoro-11-methyl-2,3,4,5-tetrahydro-1H-azepino[4,5-b]quinoline;
7-cyclohexyloxy-10-fluoro-11-methyl-2,3,4,5-tetrahydro-1H-azepino[4,5-b]quinoline;
10-chloro-7-cyclopropyl-11-methyl-2,3,4,5-tetrahydro-1H-azepino[4,5-b]quinoline;
7-cyclohexyloxy-10-fluoro-2,3,4,5-tetrahydro-1H-azepino[4,5-b]quinoline;
7-chloro-10-isopropoxy-11-methyl-2,3,4,5-tetrahydro-1H-azepino[4,5-b]quinoline;
7-chloro-10-cyclohexyloxy-2,3,4,5-tetrahydro-1H-azepino[4,5-b]quinoline; and
7-chloro-10-cycloheptyloxy-11-methyl-2,3,4,5-tetrahydro-1H-azepino[4,5-b]quinoline;
and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and test-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of "alkyl" and means a saturated carbocyclic ring having a specified number of carbon atoms. Examples of cycloalkyl include cyclopropyl, cyclobutyl, cyclopentyl, cyclohexyl, and cycloheptyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "cycloalkyloxy" is a subset of "alkoxy" and means a saturated carbocyclic ring alkoxide having a specified number of carbon atoms. Examples of cycloalkyloxy include cyclopropyloxy, cyclobutyloxy, cyclopentyloxy, cyclohexyloxy, and cycloheptyloxy, and the like.

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethyl amino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfaranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3$, $CF_3CH_2$, $CF_3O$, and $CF_3CH_2O$).

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist, as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, M-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of modulation and, in particular, selective modulation of the 5-$HT_{2C}$ receptor in a patient, such as a mammal, in need of such modulation comprising the administration of an effective amount of the compound. The compounds of the present invention are therefore useful to control, prevent, and/or treat conditions responsive to the selective modulation of the 5-$HT_{2C}$ receptor.

Thus, one aspect of the present invention concerns a method for the treatment or prevention of obesity in a mammal in need thereof, which comprises administering to said mammal a therapeutically or prophylactically effective amount of a compound in accordance with structural formula I or a pharmaceutically acceptable salt thereof.

A second aspect a method for the treatment or prevention of obesity in a mammal in need thereof, by decreasing food intake, inducing satiety, or otherwise controlling weight gain, which comprises administering to said mammal a therapeutically or prophylactically effective amount of a compound in accordance with structural formula I or a pharmaceutically acceptable salt thereof.

A third aspect of the present invention concerns a method of treating or preventing obesity-related disorders in a mammal in need thereof comprising administering to the mammal a therapeutically or prophylactically effective amount of a compound in accordance with structural formula I or a pharmaceutically acceptable salt thereof. Included among such obesity-related disorders are Type 2 diabetes, insulin resistance, dyslipidemia, atherosclerosis, and Metabolic Syndrome.

A fourth aspect of the invention concerns a method of treating Metabolic Syndrome and its sequelae in a mammal in need of such treatment comprising administering to said mammal a therapeutically effective amount of a compound in accordance with structural formula I or a pharmaceutically acceptable salt thereof. The sequelae of the Metabolic Syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammal in need of such treatment comprising administering to said mammal a therapeutically effective amount of a compound in accordance with structural formula I or a pharmaceutically acceptable salt thereof.

A sixth aspect of the invention concerns a method of treating atherosclerosis in a mammal in need of such treatment comprising administering to said mammal a therapeutically effective amount of a compound in accordance with structural formula I or a pharmaceutically acceptable salt thereof.

A seventh aspect of the invention concerns a method of treating certain CNS-related disorders in a mammal in need of such treatment comprising administering to said mammal a therapeutically effective amount of a compound in accordance with structural formula I or a pharmaceutically acceptable salt thereof. Included is such CNS-related disorders are epilepsy, urinary incontinence, depression, schizophrenia, and obsessive-compulsive disorder.

The intended target for treatment with a compound of the present invention is a mammal. One embodiment of the term "mammal" is a "human," said human being either male or female. The compounds of the present invention are also useful for treating or preventing obesity and obesity-related disorders in cats and dogs. As such, the term "mammal" includes companion animals, such as cats and dogs. The term "mammal in need thereof" refers to a mammal that is need of treatment or prophylaxis as determined by a researcher, veterinarian, medical doctor, or other clinician.

The present invention is further directed to a method for the manufacture of a medicament for modulation of the 5-$HT_{2C}$ receptor in mammals comprising combining a compound of the present invention with a pharmaceutically acceptable carrier or diluent. More particularly, the present invention is directed to the use of a compound of structural formula I in the manufacture of a medicament for use in treating a condition selected from the group consisting of obesity, Type 2 diabetes, insulin resistance, Metabolic Syndrome, a lipid disorder, and a CMS-related disorder.

The subject treated in the present methods is generally a mammal, preferably a human, male or female, in whom modulation of the 5-$HT_{2C}$ receptor is desired. The term "therapeutically effective amount" means the amount of the subject compound that will elicit the biological or medical response of a tissue, system, animal or human that is being sought by the researcher, veterinarian, medical doctor or other clinician.

The term "composition" as in "pharmaceutical composition" is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and/or "administering a" compound should be understood to mean providing a compound of the invention or a prodrug of a compound of the invention to the individual in need of treatment.

The utility of the compounds in accordance with the present invention as ligands and, in particular, as selective ligands of the $5HT_{2C}$ receptor may be demonstrated by the following assays.

By a 5-HT receptor "agonist" is meant an endogenous or drug substance or compound that can interact with a 5-HT receptor and initiate a pharmacological or biochemical response characteristic of 5-HT receptor. An agonist may be a full or partial agonist. By a 5-HT receptor "antagonist" is meant a drug or a compound that inhibits the 5-HT receptor-associated responses induced by an agonist. The "agonistic" and "antagonistic" properties of the compounds of the present invention were measured in the functional assays described below. The functional assays discriminate a 5-HT receptor agonist from a 5-HT receptor antagonist. The compounds of the present invention are agonists of the $5$-$HT_{2C}$ receptor, and, in particular, are selective agonists of the $5$-$HT_{2C}$ receptor over both the $5$-$HT_{2A}$ and $5$-$HT_{2B}$ receptors.

By "binding affinity" is meant the ability of a compound/drug to bind to its biological target, in the present instance, the ability of a compound of structural formula I to bind to a 5-HT receptor. Binding affinities of the compounds of the present invention for the $5$-$HT_{2A}$, $5$-$HT_{2B}$, and $5$-$HT_{2C}$ receptors were measured in the binding assay described below and are expressed as $IC_{50}$'s.

"Efficacy" describes the relative intensity of response which different agonists produce even they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events which, from the binding of the drug to the receptor, leads to the desired biological effect.

The functional activities, expressed as $EC_{50}$'s, and the "agonists efficacy" for the compounds of the present, invention at a particular concentration were determined in accordance to the functional assay described below.

1. Functional Assay:
    (a) Cell Culture for the Human $5$-$HT_{2A}$, Human $5$-$HT_{2B}$, and Human $5$-$HT_{2C}$ Receptors:
    CHO cells stably expressing the human $5$-$HT_{2A}$, human $5$-$HT_{2B}$, and human $5$-$HT_{2C}$ receptors were purchased from PerkinElmer (Waltham, Mass.). Cells were grown in advance DMEM/F12, 1% dialyzed fetal bovine serum, 2 mM L-glutamine, 100 units/mL penicillin, 1 mg/mL streptomycin, and 0.4 mg/ml Geneticin at 37° C. in 5% $CO_2$ atmosphere.

(b) Calcium Mobilization Assays:
    Cells were seeded in black clear-bottom 384-well plates at a density of 10,000 cells/well and incubated overnight at 37° C. in 5% $CO_2$/95% atmosphere. After removing medium, cells were loaded with modified HBSS buffer (137.9 mM NaCl, 5.3 mM KCl, 5.5 mM glucose, 20 mM Hepes, 0.49 mM $MgCl_2$, 1.26 mM $CaCl_2$, 0.41 mM $MgSO_4$, 0.33 mM $Na_2HPO_4$, and 0.44 mM $KH_2PO_4$) containing the FLIPR Calcium 4 dye (Molecular Devices, CA) and probenecid (2.5 μM) and incubated at 37° C. for 60 min, according to the manufacturer's instructions. Compounds were diluted in HBSS buffer containing 6% DMSO as six folds. Final DMSO concentration in the assay was 1%. The dose-response of agonist-stimulated $Ca^{2+}$ flux was measured on a Fluorometric Imaging Plate Reader (FLIPR Tetra) (Molecular Devices, CA).

(c) Data Analysis:
    Data were analyzed by nonlinear least squares curve fitting using GraphPad Prism 5.0 software (GraphPad Software, CA). Agonist stimulation in FLIPR assay was fitted to sigmoidal dose response curves using the equation Y=Bottom+(Top-Bottom)/(1+10^((Log $EC_{50}$-X)*Hill Slope)), where X is the logarithm of concentration of compounds. Y is the fluorescent response, $EC_{50}$ is the concentration of compound producing 50% of maximum response. Maximum responses (Emax) of compounds were calculated based on % of stimulation relative to the response of α-methyl-5HT (100%). $EC_{50}$'s are representative of two or three separate experiments performed in triplicates.

The compounds of structural formula I, particularly the compounds of the present invention denoted as non-limiting specific Examples below, exhibited $EC_{50}$'s in the range of about 1 nM to about 500 nM, against the human $5$-$HT_{2C}$ receptor. The functional activity of representative, but not limiting, examples of the present invention, against the human $5$-$RT_{2C}$ receptor are given below:

| Example | Functional assay $5$-$HT_{2C}$ ($EC_{50}$) |
|---|---|
| (structure with Cl, cyclopropyl, NH, fused ring system) | <1 nM |
| (structure with F, F, cyclopropyl, NH, fused ring system) | <5 nM |

| Example | Functional assay 5-HT$_{2C}$ (EC$_{50}$) |
|---|---|
| (structure: Cl, CH₃, cyclopropyl, tricyclic azepine) | <15 nM |
| (structure: Cl, F, cyclopropyl, tricyclic azepine) | <5 nM |
| (structure: cyclohexyloxy, Cl, tricyclic azepine) | <50 nM |
| (structure: cyclohexyloxy, CH₃, Cl, tricyclic azepine) | <5 nM |
| (structure: F, F, cyclopropyl, tricyclic azepine) | <5 nM |
| (structure: F, CH₃, F, cyclopropyl, tricyclic azepine) | <5 nM |
| (structure: F, CH₃, cycloheptyloxy, tricyclic azepine) | <10 nM |
| (structure: 3-fluorophenoxy, Cl, tricyclic azepine) | <20 nM |
| (structure: F, CH₃, F, cyclopropyl, tricyclic azepine) | <5 nM |
| (structure: F, CH₃, cyclohexyloxy, tricyclic azepine) | <10 nM |

The functional activity of the compounds of the present invention at the human 5-HT$_{2C}$ receptor was characterized by an EC$_{50}$ at least 2-fold lower than the functional activity at the human 5-HT$_{2A}$ and 5-HT$_{2B}$ receptors. In another aspect, the functional activity of the compounds of the present invention at the human 5-HT$_{2C}$ receptor was characterized by an EC$_{50}$ at least 10-fold lower than the functional activity at the human 5-HT$_{2A}$ and 5-HT$_{2B}$ receptors. In a third aspect, the functional activity of the compounds of the present invention at the human 5-HT$_{2C}$ receptor was characterized by an EC$_{50}$ at least 100-fold lower than the functional activity at the human 5-HT$_{2A}$ and 5-HT$_{2B}$ receptors. In a fourth aspect, the functional activity of the compounds of the present invention at the human 5-HT$_{2C}$ receptor was characterized by an EC$_{50}$ at least 1000-fold lower than the functional activity at the human 5-HT$_{2A}$ and 5-HT$_{2B}$ receptors.

II. Binding Assay:

The binding affinities, expressed as IC$_{50}$'s, of the compounds of the present invention for the 5-HT receptors were determined using radioligand binding assays performed with membrane preparation, test compounds, and a fixed concentration of radiolabeled agonist [$^{125}$I]DOI.

(a) Membrane Preparation:

CHO cells expressing the human 5-HT$_{2A}$, human 5-HT$_{2B}$, and human 5-HT$_{2C}$ receptors were washed twice with cold PBS, scraped off the plates, and centrifuged at 1000×g for 5 min. Cells were resuspended in ice-cold 10 mM Tris HCl, pH 7.4, containing 5 mM EDTA and protease inhibitor cocktail tablets (Roche Molecular Biochemicals). After incubation on ice for 10 min, the cells were homogenized with a dounce homogenizer or a polytron tissue grinder, and centrifuged at 1000×g for 10 min at 4° C. The resulting supernatant was centrifuged at 32,000×g for 30 min at 4° C. The membrane pellets were resuspended in 50 mM Tris HCl, pH 7.4, and stored at −80° C. until use. Protein concentration was determined by the Bradford method (Bio-Rad Laboratories, CA).

(b) Compound Dilutions:

Serial dilutions of test compounds were performed in DMSO as 200×. Compounds were subsequently diluted 100-fold in the assay buffer (50 mM Tris HCl, pH 7.5, 4 mM CaCl$_2$, 0.1% ascorbic acid, and 10 µg/ml saponin) and dispensed onto the test plate.

Assays were carried out in 96-well polypropylene plates containing 50 µL of test compounds at increasing concentrations, 25 µL of radiolabeled agonist [$^{125}$I]DOI (final concentrations: 0.4 nM for 5-HT$_{2A}$, 0.2 nM for 5-HT$_{2B}$, and 0.35 nM for 5-HT$_{2C}$) and 25 µL of membrane preparation (0.5 µg/well for 5-HT$_{2A}$ and 5-HT$_{2B}$, 2.5 µg/well for 5-HT$_{2C}$). Nonspecific binding was defined by the addition of 10 µM mianserin for the 5-HT$_{2C}$ receptor binding, 10 µM spiperone for the 5-HT$_{2A}$ receptor binding, or 10 µM methylsergide for the 5-HT$_{2B}$ receptor binding. The plate was incubated for 60 min at 25° C. in a water bath and then filtered over GF/B (5-HT$_{2A}$ and 5-HT$_{2C}$) or GF/C (5-HT$_{2B}$) filters (Perkin Elmer, MA) presoaked in 0.5% polyethyleneimine (PEI) for 2 h at room temperature with a Filtration unit (PerkinElmer, MA). The filters were washed 3 times with 0.5 ml, of ice-cold assay buffer, 50 µL of Microscint 20 (PerkinElmer, MA) was added and the plate was incubated for 15 min on an orbital shaker and then counted with a TopCount™ (PerkinElmer, MA) or MicroBeta™ (PerkinElmer, MA) for 1 min/well.

(c) Data Analysis:

Data were analyzed by nonlinear least squares curve fitting using GraphPad Prism 5.0 software (GraphPad Software, CA). The $K_D$ and $B_{max}$ for saturation were derived from the equation $RL=R_t L/(K_D+L)$, where RL is concentration of receptor-bound ligand at equilibrium, L is the free ligand concentration, and $R_t$ is the total receptor concentration (i.e., $B_{max}$). For competition binding experiments, IC$_{50}$ values (the concentration of compound producing 50% inhibition of specific binding) were derived from fitting the data to a 4-parameter logistic equation $Y=\text{Bottom}+(\text{Top}-\text{Bottom})/(1+10^{(X-\log \text{IC}_{50})})$, where X is the logarithm of concentration of compounds, Y is the specific binding, cpm. Apparent K$_i$ values were calculated using the Cheng-Prussof equation of $K_i=\text{IC}_{50}/(1+(L/K_D))$, where L is the ligand concentration.

III. In Vivo Assay:

The in vivo efficacy of compounds of the present invention was assessed for their ability to regulate feeding behavior by recording food consumption in food deprived animals in accordance with the following assay.

Male Sprague Dawley rats weighing between 300 and 400 grams were acclimated for one week and baseline consumption recorded for three days. The animals were food deprived overnight with continued free access to water. A compound of structural formula (I) or vehicle was administered to the rats orally (PO) in the morning to a maximum of 30 mg/kg. Food was returned after administration of the compound. Food eaten was measured at 2 and 4 h after closing with compound. Efficacy was assessed by comparing the amount of food eaten in the compound-treated animals as compared to those treated with vehicle. The positive control rimonobant (a CB1 inverse agonist, dosed at 3 mg/kg, PO) afforded about 40% to 45% decrease in food intake based on grams of food intake. The ability of a compound of the present invention to reduce food intake correlated with its functional activity against the 5-HT$_{2C}$ receptor and its ability to penetrate into the brain. Thus, the more potent the compound and the more of it that was demonstrated to be in the brain led to greater efficacy in the reduction of food intake.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred, particularly in combination with a pharmaceutically acceptable carrier. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will, generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Examples of other active ingredients that may be administered in combination with a compound of Formula I, and either administered separately or in the same pharmaceutical composition, include, but are not limited to:

(1) other antiobesity compounds;
(2) dipeptidyl peptidase-IV (DPP-4) inhibitors;
(3) insulin sensitizers, including (i) biguanides, such as metformin and its pharmaceutically acceptable salts, in particular, metformin hydrochloride, and extended-release formulations thereof, such as Glumetza®, Fortamet®, and GlucophageXR®; and (ii) protein tyrosine phosphatase-1B (PTP-1B) inhibitors;
(4) sulfonylurea and non-sulfonylurea insulin secretogogues, such as tolbutamide, glyburide, glipizide, glimepiride, mitiglinide, and meglitinides, such as nateglinide and repaglinide;
(5) α-glucosidase inhibitors (such as acarbose, voglibose and miglitol);
(6) incretin mimetics, such as GLP-1, GLP-1 analogs, derivatives, and mimetics (See for example, WO 2008/011446, U.S. Pat. No. 5,545,618, U.S. Pat. No. 6,191,102, and U.S. Pat. No. 56,583,111); and GLP-1 receptor agonists, such as oxyntomodulin and its analogs and derivatives (See for example, WO 2003/022304, WO 2006/134340, WO 2007/100535), glucagon and its analogs and derivatives (See for example, WO 2008/101017), exenatide, liraglutide, taspoglutide, albiglutide, AVE0010, CJC-1134-PC, NN9535, LY2189265, LY2428757, and BIM-51077, including intranasal, transdermal, and once-weekly formulations thereof, such as exenatide QW;
(7) LDL cholesterol lowering agents such as (i) HMG-CoA reductase inhibitors (lovastatin, simvastatin, pravastatin, cerivastatin, fluvastatin, atorvastatin, pitavastatin, and rosuvastaiin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;
(8) HDL-raising drugs, such as niacin or a salt thereof and extended-release versions thereof and nicotinic acid receptor agonists;
(9) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as altskiren), beta blockers (such as and calcium channel blockers (such as;
(10) glucokinase activators (GKAs), such as LY2599506;
(11) inhibitors of 11β-hydroxysteroid dehydrogenase type 1, such as those disclosed in U.S. Pat. No. 6,730,690; WO 03/104207; and WO 04/058741;
(12) inhibitors of cholesteryl ester transfer protein (CETP), such as torcetapib and anacetrapib;
(13) inhibitors of fructose 1,6-bisphosphatase, such as those disclosed in U.S. Pat. Nos. 6,054,587; 6,110,903; 6,284,748; 6,399,782; and 6,489,476;
(14) AMP-activated Protein Kinase (AMPK) activators;
(15) inhibitors of glucose uptake, such as sodium-glucose co-transporter (SGLT) inhibitors and its various isoforms, such as SGLT-1; SGLT-2, such as dapagliflozin, canagliflozin, empagliflozin, dapagliflozin, ipragliflozin, topogliflozin and remogliflozin; and SGLT-3.

Dipeptidyl peptidase-IV (DPP-4) inhibitors that can be used in combination with compounds of Formula I include, but are not limited to, sitagliptin (disclosed in U.S. Pat. No. 6,699,871), vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Antiobesity compounds that can be combined with compounds of Formula I include topiramate; zonisamide; naltrexone; phentermine; bupropion; the combination of bupropion and naltrexone (CONTRAVE®); the combination of bupropion and zonisamide; the combination of topiramate and phentermine (QYSMIA®); fenfluramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists; CB1 receptor inverse agonists and antagonists (such as rimonabant and taranabant); $β_3$ adrenergic receptor agonists; methionine-aminopeptidase 2 (MetAP2) inhibitors; ghrelin antagonists; bombesin receptor agonists (such as bombesin receptor subtype-3 agonists); histamine H3 receptor inverse agonists; 5-hydroxytryptamine-2c (5-$HT_2$c) agonists, such as lorcaserin; and inhibitors of fatty acid synthase (FAS). For a review of antiobesity compounds that can be combined with compounds of the present invention, see S. Chaki et al., "Recent advances in feeding suppressing agents: potential therapeutic strategy for the treatment of obesity," *Expert Opin. Ther. Patents.* 11: 1677-1692 (2001); D. Spanswick and K. Lee, "Emerging antiobesity drugs," *Expert Opin. Emerging Drugs.* 8: 217-237 (2003); J. A. Fernandez-Lopez, et al., "Pharmacological Approaches for the Treatment of Obesity," *Drugs,* 62: 915-944 (2002); and K. M. Gadde, et al., "Combination pharmaceutical therapies for obesity," *Exp. Opin. Pharmacother.,* 10: 921-925 (2009).

In another aspect of the invention, a pharmaceutical composition is disclosed which comprises:
(1) a compound of structural formula I;
(2) a compound selected from the group consisting of:
  (a) dipeptidyl peptidase IV (DPP-IV) inhibitors;
  (b) insulin sensitizers, including (i) biguanides such as metformin and phenformin, and (ii) protein tyrosine phosphatase-1B (PTP-1B) inhibitors;
  (c) sulfonylureas and other insulin secretogogues, such as tolbutamide, glyburide, glipizide, glimepiride, and meglitinides, such as nateglinide and repaglinide;
  (d) α-glucosidase inhibitors (such as acarbose and miglitol);
  (e) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;
  (f) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitor, such as avasimibe, and (viii) antioxidants, such as probucol;

(g) antiobesity compounds, such as topiramate, fenfluramine, phentermine, fixed-dose combination of phentermine and topiramate, fixed-dose combination of bupropion and naltrexone, orlistat, neuropeptide $Y_1$ or $Y_5$ antagonists, CB1 receptor inverse agonists and antagonists, $\beta_3$ adrenergic receptor agonists, melanocortin-4 receptor agonists, ghrelin antagonists, bombesin receptor agonists (such as bombesin receptor subtype-3 agonists), melanin-concentrating hormone (MCH) receptor antagonists, and methionine-aminopeptidase 2 (MetAP2) inhibitors;

(h) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(i) glucokinase activators (GKAs), such as those disclosed in WO 03/015774; WO 04/076420; and WO 04/081001; and (j) inhibitors of cholesteryl ester transfer protein (CETP), such as torcetrapib and anacetrapib; and (3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective close of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution, hi addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drag. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require modulation of the $5\text{-HT}_{2c}$ receptor, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 1.5.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing obesity or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily close or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Preparation of Compounds of the Invention

Synthetic methods for preparing the compounds of the present invention are illustrated in the following Schemes, Methods, and Examples. Starting materials are commercially available or may be prepared according to procedures known in the art or as illustrated herein. The compounds of the invention are illustrated by means of the specific examples shown below. However, these specific examples are not to be construed as forming the only genus that is considered as the invention. These examples further illustrate details for the preparation of the compounds of the present invention. Those skilled in the art will readily understand that known variations of the conditions and processes of the following preparative procedures can be used to prepare these compounds. All temperatures are in degrees Celsius unless otherwise noted. Mass spectra (MS)

were measured by electrospray ion-mass spectroscopy (ESI). $^1$H NMR spectra were recorded on Bruker instruments at 400 MHz.

LIST OF ABBREVIATIONS

Alk=alkyl
Ar=aryl
Boc=tert-butoxycarbonyl
bs=broad singlet
$CH_2Cl_2$=dichloromethane
d=doublet
dd=doublet of doublets
DBU=1,8-diazabicyclo[5.4.0]undec-7-ene
DCM=dichloromethane
DEAD=diethyl azodicarboxylate
DMF=N,N'-dimethylformamide
DMSO=dimethyl sulfoxide
ESI=electrospray ionization
EtOAc=ethyl acetate
EtOH=ethyl alcohol
h=hours
HOAc=acetic acid
LiOH=lithium hydroxide
m=multiplet.
MeCN=acetonitrile
MeOH=methyl alcohol
$MgSO_4$=magnesium sulfate
min=minutes
MS=mass spectroscopy
NaCl=sodium chloride
NaOH=sodium hydroxide
$Na_2SO_4$=sodium sulfate
NMR=nuclear magnetic resonance spectroscopy
PG=protecting group
Ph=phenyl
rt=room temperature
s=singlet
t=triplet
TFA=trifluoroacetic acid
THF=tetrahydrofuran The compounds of the present invention were prepared following general methods A-C detailed below.

Method A: General Method of Synthesis of 2,3,4,5-tetrahydro-1H-azepino[4,5-b]quinoline Method A is outlined in Scheme 1. The starting amino aldehyde A (purchased from commercial sources or prepared using published literature procedures) is mixed with tert-butyl 4-oxo-azepane-1-carboxytate and base (EtONa or MeONa) in EtOH under reflux conditions affording tricyclic intermediate B. The title compound C is then obtained by stirring intermediate B with excess TFA in DCM (to give the trifluoroacetate salt) or HCl in dioxane (to give the hydrochloride salt) at room temperature for 1-3 h. The reaction sequence may be modified somewhat with different substituents $R^1$, $R^2$, $R^3$, and $R^4$.

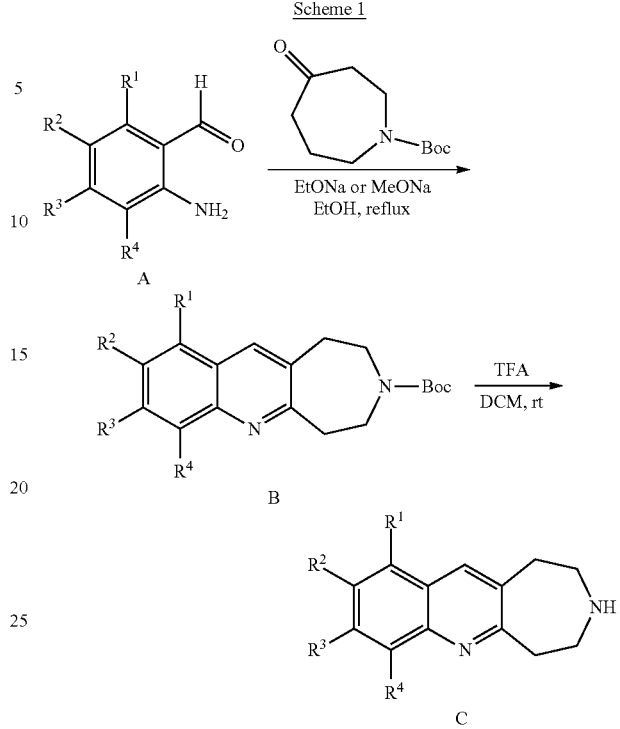

Scheme 1

Method B: General Method of Synthesis of 11-methyl-2,3,4,5-tetrahydro-1H-azepino[4,5-b]quinoline Method B is outlined in Scheme 2. The starting aniline D (purchased from commercial sources or prepared using published literature procedures) is mixed with 1-tert-butyl 4-ethyl-5-oxoazepane-1,4-dicarboxylate and polyphosphoric acid (PPA) in 1,4-dioxane at 120° C. affording a tricyclic intermediate which is then reacted with BOC anhydride to give intermediate E. Treatment of intermediate E with $PBr_3$ in DMF from 0° C. to room temperature gives intermediate bromide F. Coupling reaction with dimethylzinc or 2,4,6-trimethyl-cyclotriboroxane affords intermediate G. The title compound H is then obtained by stirring compound G with excess TFA in DCM (to give the trifluoroacetate salt) or HCl in 1,4-dioxane (to give the hydrochloride salt) at room temperature for 1-3 h. The reaction sequence may be modified somewhat with different substituents $R^1$, $R^2$, $R^3$, and $R^4$.

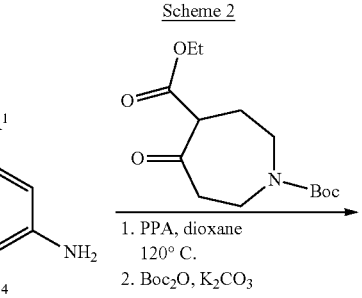

Scheme 2

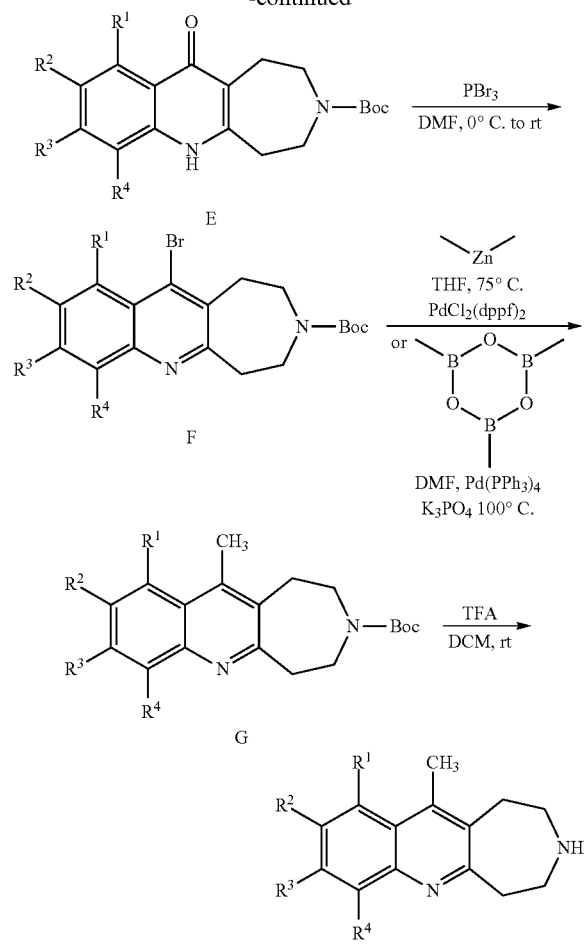

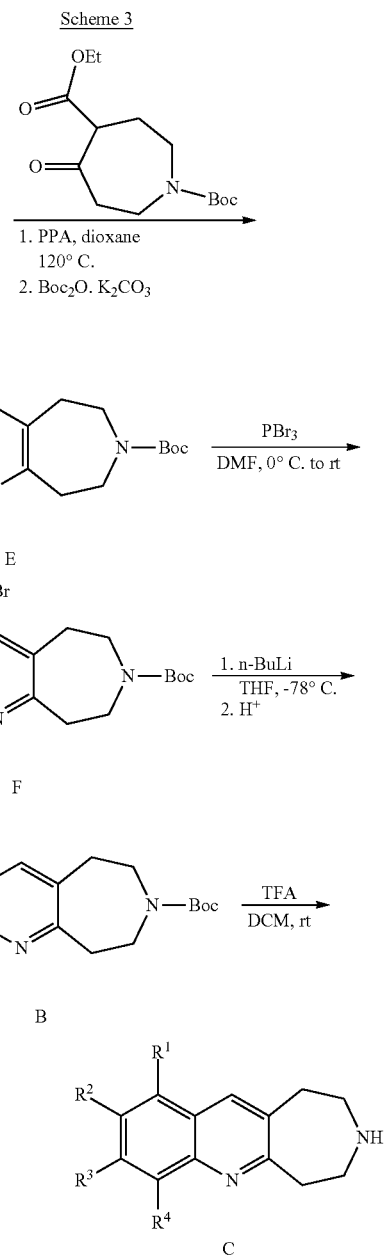

Method C: General Method of Synthesis of 2,3,4,5-tetrahydro-1H-azepino[4,5-b]quinoline Alternatively, compound C can be obtained using Method C if Method A is not accessible. Method C is outlined in Scheme 3. The starting aniline I) (purchased from commercial sources or prepared using published literature procedures) is mixed with 1-tert-butyl 4-ethyl-5-oxoazepane-1,4-dicarboxylate and polyphosphoric acid (PPA) in 1,4-dioxane at 120° C. affording a tricyclic intermediate which is then reacted with BOC anhydride to give intermediate E. Treatment of intermediate E with PBr₃ in DMF from 0° C. to room temperature gives intermediate bromide F. Treatment of F with n-BuLi at −78° C. in THF, followed by quenching with water affords the intermediate B. The title compound C is then obtained by stirring intermediate B with excess TFA in DCM (to give the trifluoroacetate salt) or HO in dioxane (to give the hydrochloride salt) at room temperature for 1-3 h. The reaction sequence may be modified somewhat with different R¹, R², R³, and R⁴.

The following numbering system on the azepino[4,5-d] quinoline nucleus was used to name the compounds of the present invention:

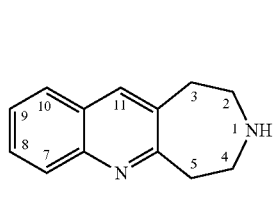 [SMILES: c1ccc2nc3c(cc2c1)CCNCC3]

The following Examples are provided to illustrate the invention and are not intended to be construed as limiting the scope of the invention in any manner.

EXAMPLE 1
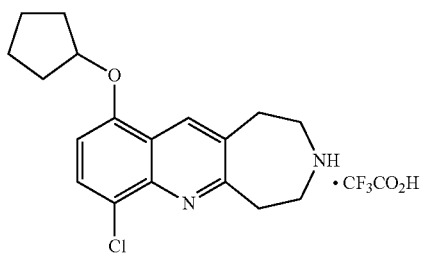
7-Chloro-10-(cyclopentyloxy)-2,3,4,5-tetrahydro-1H-azepino[4,5-b]quinoline trifluoroacetate salt
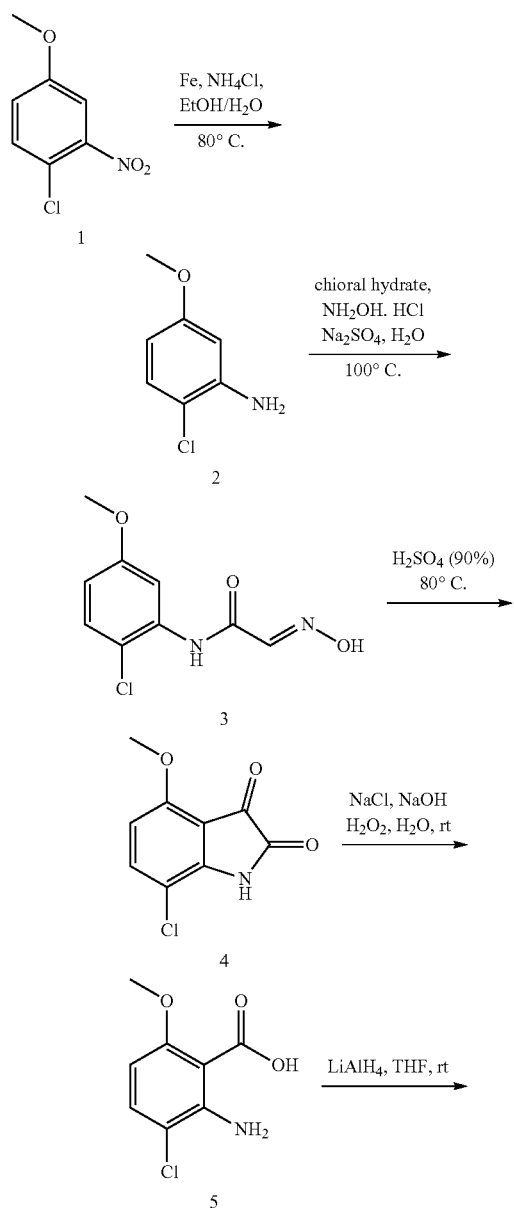
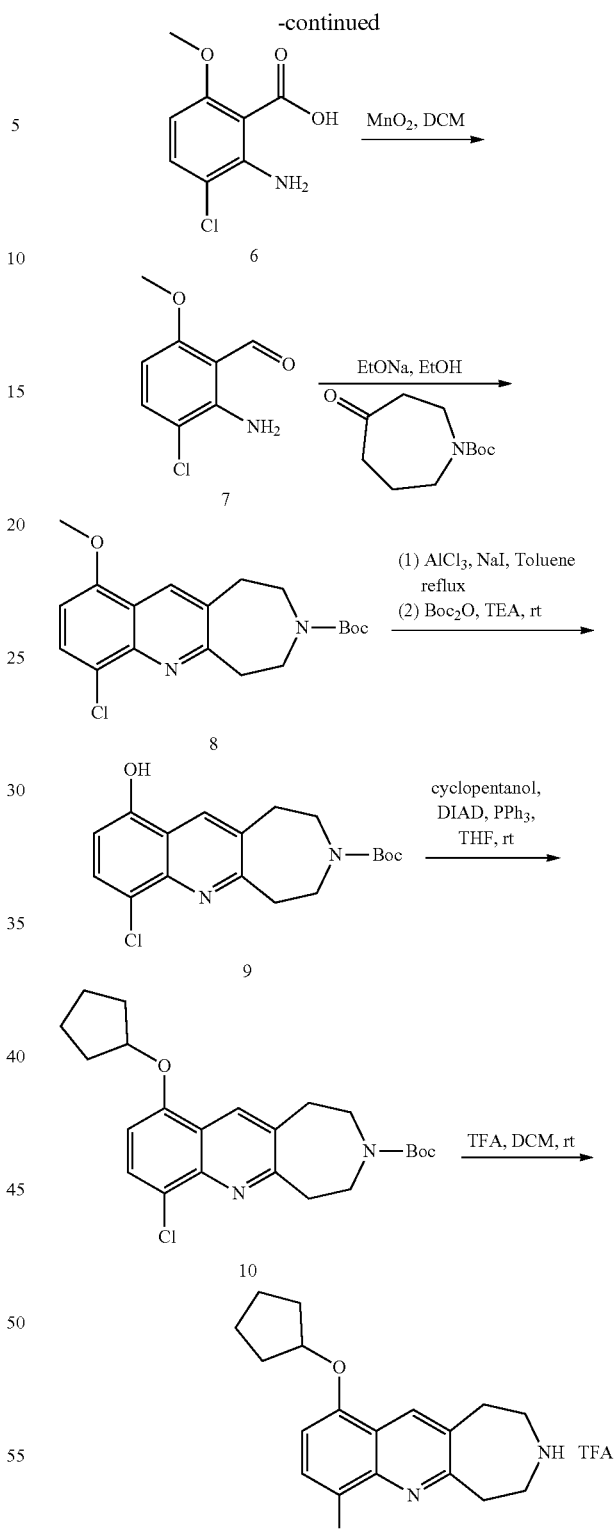
Step 1: 2-Chloro-5-methoxyanilino (2)
To a mixture of 1-chloro-4-methoxy-2-nitrobenzene (1, 40 g, 213 mmol) and ammonium chloride (45.6 g, 853 mmol) in ethanol (500 mL) and water (100 ml) was slowly added iron powder (47.6 g, 853 mmol) in portions at 80° C. The mixture was stirred at reflux temperature for 3 h. After the starting material was consumed, the reaction mixture was concentrated under reduced pressure and the residue was diluted with ethyl acetate (200 mL), filtered and the filtrate was washed with saturated brine solution. The organic phase was dried over anhydrous sodium sulfate, concentrated in vacuo to give the title compound which was used in the next step without further purification.

Step 2: N-(2-Chloro-5-methoxyphenyl)-2-(hydroxy-imino)acetamide (3)

To a solution of 2-chloro-5-methoxyaniline (2, 27 g, 171 mmol, from Step 1) in 12 M hydrochloric acid (15 mL) and water (600 mL) was added a solution of sodium sulfate (268 g, 1.89 mol) and chloral hydrate (39.7 g, 2.40 mmol) in water (200 mL). Hydroxylamine hydrochloride (42.9 g, 617 mmol) in water (200 mL) was then added, the resulting solution was stirred at 100° C. for 2 h. After the starting material was consumed, the reaction mixture was cooled to rt, filtered, and washed with water. The resulting solid was dissolved in ethyl acetate (200 mL), the solution was washed with brine (200 mL), the organic phase was dried over anhydrous sodium sulfate, and the solvent was removed under diminished pressure to give the title compound as a yellow solid.

Step 3: 7-Chloro-4-methoxyindoline-2,3-dione (4)

N-(2-Chloro-5-methoxyphenyl)-2-(hydroxyimino)acetamide (3, 28 g, 122 mmol, from Step 2) was added to 90% aqueous sulfuric acid (300 mL) by portion at 60° C. to about 80° C. The mixture was stirred at 93° C. for 1 h. After the starting material was consumed, the reaction mixture was poured into ice-water, filtered, washed with water, and dried over anhydrous sodium sulfate. The resulting solid was recrystallized from ethyl acetate to give the title compound as a red solid, $^1$H NMR (400 MHz, CDCl$_3$): δ 7.96 (br, 1H), 7.47 (d, J=9.2 Hz, 1H), 6.60 (d, J=9.2 Hz, 1H), 3.99 (s, 3H).

Step 4: 2-Amino-3-chloro-6-methoxybenzoic acid (5)

A solution of 7-chloro-4-methoxyindoline-2,3-dione (4, 18 g, 85 mmol, from Step 3), sodium chloride (12 g, 205 mmol) and sodium hydroxide (15 g, 375 mmol) in water (200 mL) was stirred at rt for 0.5 h. 30% aqueous Hydrogen peroxide (20 mL, 194 mmol) was then slowly added at 0° C. After the reaction was over, 3M hydrochloric acid was added to adjust the pH to 3-5, and the product was extracted with DCM (200 mL), dried over anhydrous sodium sulfate, and filtered. The filtrate was concentrated in vacuo to give the title compound as a yellow solid.
$^1$H NMR (400 MHz, CDCl$_3$): δ 11.21 (bs, 1H), 7.35 (d, J=8.8 Hz, 1H), 6.93 (bs, 2H), 6.21 (d, J=8.8 Hz, 1H), 4.03 (s, 3H).

Step 5: (2-Amino-3-chloro-6-methoxyphenyl)methanol (6)

To a solution of lithium, aluminum hydride (3.8 g, 100 mmol) in THF (100 mL) was added 2-amino-3-chloro-6-methoxybenzoic acid (5, 10 g, 50 mmol, from Step 4) dropwise at 0° C. The mixture was stirred at rt for 1 h. After the starting material was consumed, water was added dropwise to quench-the reaction. The mixture was stirred at rt for 0.5 h, then sodium sulfate was added, and the mixture was stirred at rt for additional 10 min. The mixture was then filtered and the filtrate was concentrated in vacuo to give the title compound as a brown oil.

Step 6: 2-Amino-3-chloro-6-methoxybenzaldehyde (7)

To a solution of (2-amino-3-chloro-6-methoxyphenyl)methanol (6, 8.5 g, 45 mmol, from Step 5) in DCM (100 mL) was added manganese (IV) oxide (39 g, 450 mmol) at rt. The mixture was stirred at rt for 3 h. After the starting material was consumed, the reaction mixture was filtered and the resulting solid was subjected to purification by column chromatography (silica gel, ethyl acetate:petroleum ether=1:10) to give the title compound as a yellow solid. $^1$H NMR (400 MHz, CDCl$_3$): δ 10.40 (s, 1H), 6.93 (bs, 2H), 6.11 (d, J=8.8 Hz, 1H), 3.86 (s, 3H).

Step 7: 7-Chloro-10-methoxy-2,3,4,5-tetrahydro-1H-azepino[4,5-b]quinoline-3-carboxylic acid tert-butyl ester (8)

Sodium methanol ate (1.2 g, 22 mmol) was added to a solution of 2-amino-3-chloro-6-methoxybenzaldehyde (7, 3.8 g, 20.5 mmol, from Step 6) and tert-butyl 4-oxo-azepane-1-carboxylate (4.37 g, 20.5 mmol) dissolved in ethanol (50 ml). The solution was heated to 90° C. for 1 h. The solvent was removed under reduced pressure and the resulting residue was partitioned between ethyl acetate (20 mL) and brine (20 mL). The organic layer was then dried over sodium sulfate, filtered, concentrated in vacuo and the crude product was purified by column chromatography (silica gel, ethyl acetate:petroleum ether=1:10) to give the title compound as a white solid. MS (ESI) m/z: calcd 363.14 (M+H), found 363.1.

Step 8: 7-Chloro-10-hydroxy-2,3,4,5-tetrahydro-1H-azepino[4,5-b]quinoline-3-carboxylic acid tert-butyl ester (9)

To a solution of 7-chloro-10-methoxy-2,3,4,5-tetrahydro-1H-azepino[4,5-b]quinoline-3-carboxylic acid tert-butyl ester (8, 0.82 g, 2.26 mmol, from Step 7) in toluene (5 mL) were added aluminum trichloride (1.51 g, 11.3 mmol) and sodium iodide (1.69 g, 11.3 mmol). The reaction mixture was stirred at 110° C. overnight. After the starting material was consumed, sodium bicarbonate was added to adjust the pH to 5-8, and the mixture was extracted with DCM (10 mL). The organic layer was dried over anhydrous sodium sulfate and filtered. To the filtrate were added triethylamine (0.42 g, 4.10 mmol) and di-tert-butyl dicarbonate (0.671 g, 3.08 mmol). The mixture was stirred at rt for 3 h. 1M Hydrochloric add was then added to adjust the pH to 4-6, and the mixture was extracted with DCM. The organic layer was dried over anhydrous sodium sulfate, filtered, and concentrated in vacuo. The crude product was purified by column chromatography (silica gel, eluting with 0% to 20% EtOAc in petroleum ether) to give the title compound as a white solid. MS (ESI) m/z: calcd 349.12 (M+H), found 349.1.

Step 9: 7-Chloro-10-(cyclopentyloxy)-2,3,4,5-tetrahydro-1H-azepino[4,5-b]quinoline-3-carboxylic acid tert-butyl ester (10)

A mixture of 7-chloro-10-hydroxy-2,3,4,5-tetrahydro-1H-azepino[4,5-b]quinoline-3-carboxylic acid tert-butyl ester (9, 0.40 g, 1.15 mmol, from Step 8), cyclopentanol (0.15 g, 1.72 mmol) and triphenylphosphine (0.90 g, 3.4 mmol) in THF (5.0 mL) was stirred at rt for 0.5 h. Diisopropyl azodicarboxylate (0.464 g, 2.29 mmol) was then added with cooling in an ice bath, and the mixture was stirred at rt for 2 h. After the starting material was consumed, the reaction mixture was quenched with water, and the product was extracted with ethyl acetate (20 mL). The organic layer was dried over anhydrous sodium sulfate, filtered, and concentrated in vacuo. The crude product was purified by column chromatography (silica gel, ethyl acetate:petroleum ether=1:15) to give the title compound as a light-yellow solid. $^1$H NMR (400 MHz, CDCl$_3$): δ 8.24 (s, 1H), 7.61 (d, J=8.4 Hz, 1H), 6.72 (d, J=8.4 Hz, 1H), 4.93-4.91 (m, 1H), 3.75-3.61 (m, 4H), 3.40-3.35 (m, 2H), 3.10-3.02 (m, 2H), 2.10-1.90 (m, 4H), 1.87-1.80 (m, 2H), 1.70-1.65 (m, 2H), 1.51 (s, 9H).

Step 10: 7-(Chloro-10-(cyclopentyloxy)-2,3,4,5-tetrahydro-1H-azepino[4,5-b]quinoline trifluoroacetate salt (11)

To a solution of 7-chloro-10-(cyclopentyloxy)-2,3,4,5-tetrahydro-1H-azepino[4,5-b]quinoline-3-carboxylic acid tert-butyl ester (10, 0.3 g, 0.72 mmol, from Step 9) in DCM (5 mL) was added TFA (1.0 mL), and the mixture was stirred at rt for 2 h. After the starting material was consumed, the reaction mixture was concentrated in vacuo and then dried under vacuum to give the title compound as a yellow solid. $^1$H NMR (400 MHz, CD$_3$OD): δ 8.46 (s, f H), 7.72 (d, J=8.4 Hz, 1H), 6.95 (d, J=8.4 Hz, 1H), 5.05-5.00 (m, 1H), 3.61-3.58 (m, 2H), 3.48-3.37 (m, 6H), 2.09-2.04 (m, 2H), 1.97-1.86 (m, 4H), 1.80-1.65 (m, 2H), 1.51 (s, 9H); MS (ESI) m/z: calcd 316.13 (M+H), found 317.1.

EXAMPLE 2

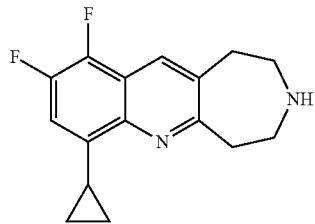

7-Cyclopropyl-9,10-difluoro-2,3,4,5-tetrahydro-1H-azepino[4,5-b]quinoline

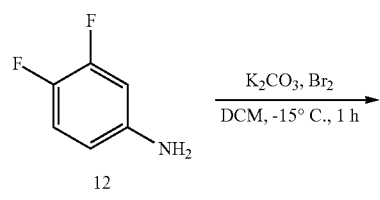

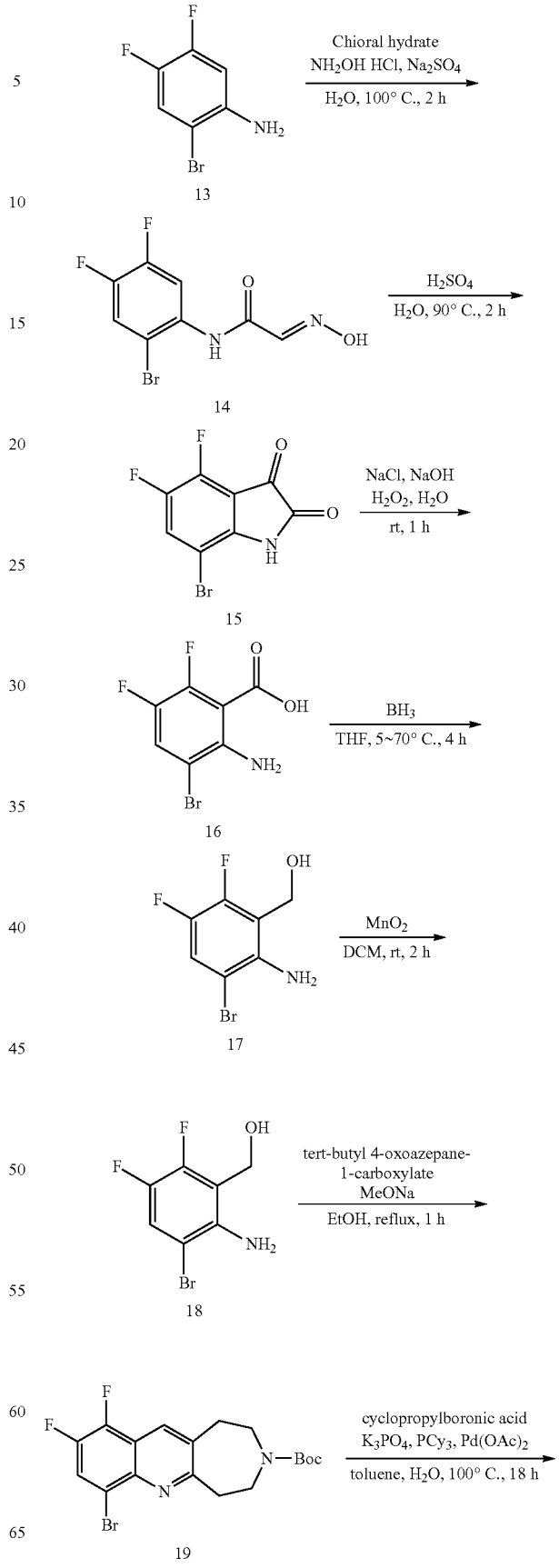

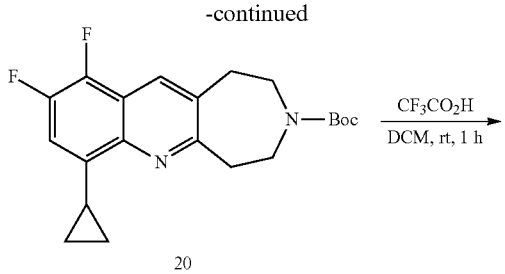

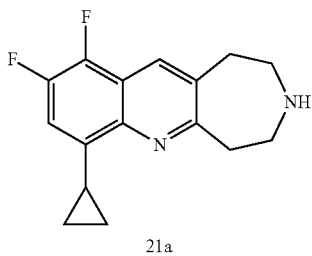

Step 1: 2-Bromo-4,5-difluoroaniline (13)

A solution of bromine (30.9 g, 194 mmol) in DCM (100 mL) was added dropwise into a suspension of 3,4-difluoroaniline (25 g, 194 mmol) and potassium carbonate (26.72 g, 194 mmol) in DCM (800 mL) at −15° C. After the addition was completed, the mixture was stirred at the same temperature for 30 min and then poured into ice water and extracted with DCM. The organic layer was washed with brine, dried over anhydrous sodium sulfate and concentrated in vacuo to give the title compound.
$^1$H NMR (400 MHz, CDCl$_3$): δ 7.24-7.22 (m, 1H), 6.60-6.55 (m, 1H), 3.99 (bs, 2H); MS (ESI): m/z: calcd 130.11 (M+H), found 130.1.

Step 2: N-(2-Bromo-4,5-difluorophenyl)-2-(hydroxyimino)acetamide (14)

To a solution of 2-bromo-4,5-difluoroaniline (13, 38 g, 183 mmol, from Step 1) in 12 N hydrochloric acid (6.0 mL) and H$_2$O (800 mL) was added sodium sulfate (247 g) and 2,2,2-trichloroethane-1,1-diol (45.3 g, 274 mmol). Hydroxylamine hydrochloride (45.7 g, 658 mmol) was then added, the resulting solution was stirred at 100° C. for 2 h. After the starting material was consumed, the mixture was cooled to rt, and the product was extracted with ethyl acetate. The organic layer was washed with brine, dried over anhydrous Na$_2$SO$_4$, filtered, and the solvent was removed in vacuo to give the title compound as a brown solid. MS (ESI) m/z: calcd 280.04 (M+H), found 280.0.

Step 3: 7-Bromo-4,5-difluoroindoline-2,3-dione (15)

N-(2-Bromo-4,5-difluorophenyl)-2-(hydroxyimino)acetamide (14, 42 g, 151 mmol, from Step 2) was added to 90% aqueous H$_2$SO$_4$ (300 mL) by portion at 60° C. to about 80° C. The mixture was stirred at 90° C. for 10 min. After the starting material was consumed, the mixture was poured into ice-water, filtered, washed with H$_2$O, and dried to give the title compound. MS (ESI) m/z calcd 263.01 (M+H), found 263.0.

Step 4: 2-Amino-3-bromo-5,6-difluorobenzoic acid (16)

A solution of 7-bromo-4,5-difluoroindoline-2,3-dione (15, 2 g, 7.63 mmol, from Step 3), NaCl (1.07 g, 18.31 mmol) and NaOH (0.8 g, 18.31 mmol) in H$_2$O (100 mL) was stirred at rt for 0.5 h. 30% Aqueous H$_2$O$_2$ (5 mL) was then added slowly, followed by an aqueous NaOH solution (0.8 g NaOH in 100 mL of water). After the starting material was consumed, 3M aqueous HCl was added to adjust pH to 3-5. The product was extracted with CH$_2$Cl$_2$, dried over anhydrous sodium sulfate, and concentrated in vacuo to give the title compound as a brown yellow solid. MS (ESI) m/z: calcd 253.01 (M+H), found 253.0.

Step 5: (2-Amino-3-bromo-5,6-difluorophenyl)methanol (17)

2-Amino-3-bromo-5,6-difluorobenzoic acid (16, 2 g, 7.94 mmol, from Step 4) was dissolved in THF (10 mL) and stirred at 5° C., then a solution of 1M BH$_3$ in dry THF (3.17 mL) was added. The resulting mixture was stirred at 70° C. for 4 h. Water was then added dropwise, followed by sodium sulfate. The mixture was stirred for 30 min, filtered, and concentrated in vacuo to give the title compound as a brow oil. MS (ESI) m/z: calcd 239.03 (M+H), found 239.0.

Step 6: 2-Amino-3-bromo-5,6-difluorobenzaldehyde (18)

To a solution of (2-Amino-3-bromo-5,6-difluorophenyl)methanol (17, 1.5 g, 6.30 mmol, from Step 5) in CH$_2$Cl$_2$ (20 mL) was added active MnO$_2$ (5.48 g) dropwise and the mixture was stirred at rt for 2 h. The mixture was filtered and the filtrate was concentrated in vacuo to afford the title compound. $^1$H NMR (400 MHz, CDCl$_3$) δ 10.28 (s, 1H), 7.56 (t, J=8.4 Hz, 1H), 6.73 (bs, 2H). MS (ESI) m/z: calcd 237.01 (M+H), found 237.0.

Step 7: 7-Bromo-9,10-difluoro-2,3,4,5-tetrahydro-1H-azepino[4,5-b]quinoline-3-carboxylic acid tert-butyl ester (19)

Sodium methanolate (1.8, 0.298 g, 5.51 mmol) was added to a solution of 2-amino-3-bromo-5,6-difluorobenzaldehyde (1.3 g, 5.51 mmol, from Step 6) and tert-butyl 4-oxo-azepane-1-carboxylate (1.175 g, 5.51 mmol) in ethanol (15 mL). The solution was heated to 70° C. for 1 h. The solvent was then removed under reduced pressure, and the resulting residue was partitioned between ethyl acetate (15 mL) and saturated brine solution (20 mL). The organic layer was then dried over sodium sulfate, filtered, and concentrated in vacuo. The crude product was purified by flash chromatography on silica gel eluting with 0-10% EtOAc in petroleum ether to afford the title compound, $^1$HNMR (400 MHz, CDCl$_3$): δ 8.12 (s, 1H), 7.86 (t, J=8.0 Hz, 1H), 3.69-3.67 (m, 4H), 3.40-3.38 (m, 2H), 3.11-3.09 (m, 2H), 1.50 (s, 9H); MS (ESI) m/z: calcd 414.26 (M+H), found 414.2.

Step 8: 7-Cyclopropyl-9,10-difluoro-2,3,4,5-tetrahydro-1H-azepino[4,5-b]quinoline-3-carboxylic acid tert-butyl ester (20)

To a mixture of 7-bromo-9,10-difluoro-2,3,4,5-tetrahydro-1H-azepino[4,5-b]quinoline-3-carboxylic acid tert-butyl ester (19, 600 mg, 1.452 mmol, from Step 7), cyclopropylboronic acid (249 mg, 2.90 mmol), K$_3$PO$_4$·H$_2$O (1.337 g, 5.81 mmol) and tricyclohexylphosphine (81 mg, 0.290 mmol) in toluene (10 mL) and water (1 mL) under a nitrogen atmosphere was added palladium diacetate (32.6 mg, 0.145 mmol). The mixture was heated at 100° C.

overnight and then cooled to rt. Water (10 mL) was then added and the mixture was extracted with EtOAc (2×15 mL). The combined organic extracts were washed with brine, dried over MgSO₄, concentrated and the crude product purified by column chromatography on silica gel eluting with 0% to 10% EtOAc in petroleum ether to give the title compound.

¹HNMR (400 MHz, CDCl₃): δ 8.07 (s, 1H), 6.83 (t, J=8.2 Hz, 1H), 3.70-3.67 (m, 4H), 3.36-3.34 (m, 2H), 3.24-3.22 (m, 1H), 3.09-3.05 (m, 2H), 1.55 (s, 9H), 1.27-1.24 (m, 2H), 0.82-0.80 (m, 2H); MS (ESI) m/z: calcd 375.42 (M+H), found 375.4.

Step 9: 7-(Cyclopropyl-9,10-difluoro-2,3,4,5-tetrahydro-1H-azepino[4,5-b]quinoline (21a)

7-Cyclopropyl-9,10-difluoro-2,3,4,5-tetrahydro-1H-azepino[4,5-b]quinoline-3-carboxylic acid tert-butyl ester (20, 340 mg, 0.908 mmol, from Step 8) was dissolved in 5:1 DCM/TFA (5 mL) and the mixture stirred at ambient temperature for 1 h. The TFA was removed by concentration in vacuo and the resulting material was partitioned between EtOAc (5 mL) and 1M aqueous K₂CO₃ (2 mL). Additional solid K₂CO₃ was added to ensure a basic aqueous layer. The EtOAc layer was then dried over Na₂SO₄, filtered, and concentrated in vacuo. The resulting residue was placed under vacuum overnight to give the title compound.

¹HNMR (400 MHz, CD₃OD): δ 8.31 (s, 1H), 7.10 (t, J=8.8 Hz, 1H), 3.58-3.55 (m, 2H), 3.49-3.43 (m, 4H), 3.39-3.34 (m, 2H), 3.20-3.18 (m, 1H), 1.16-1.13 (m, 2H), 0.85-0.83 (m, 2H); MS (ESI): calcd 275.42 (M+H), found 275.4.

EXAMPLE 3

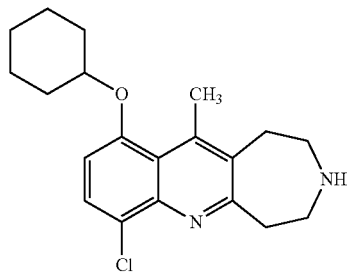 [SMILES: Cc1c2c(nc3c(Cl)ccc(OC4CCCCC4)c13)CCNCC2]

7-Chloro-10-(cyclohexyloxy)-11-methyl-2,3,4,5-tetrahydro-1H-azepino[4,5-b]quinoline

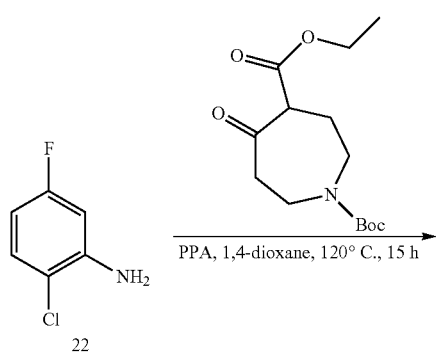

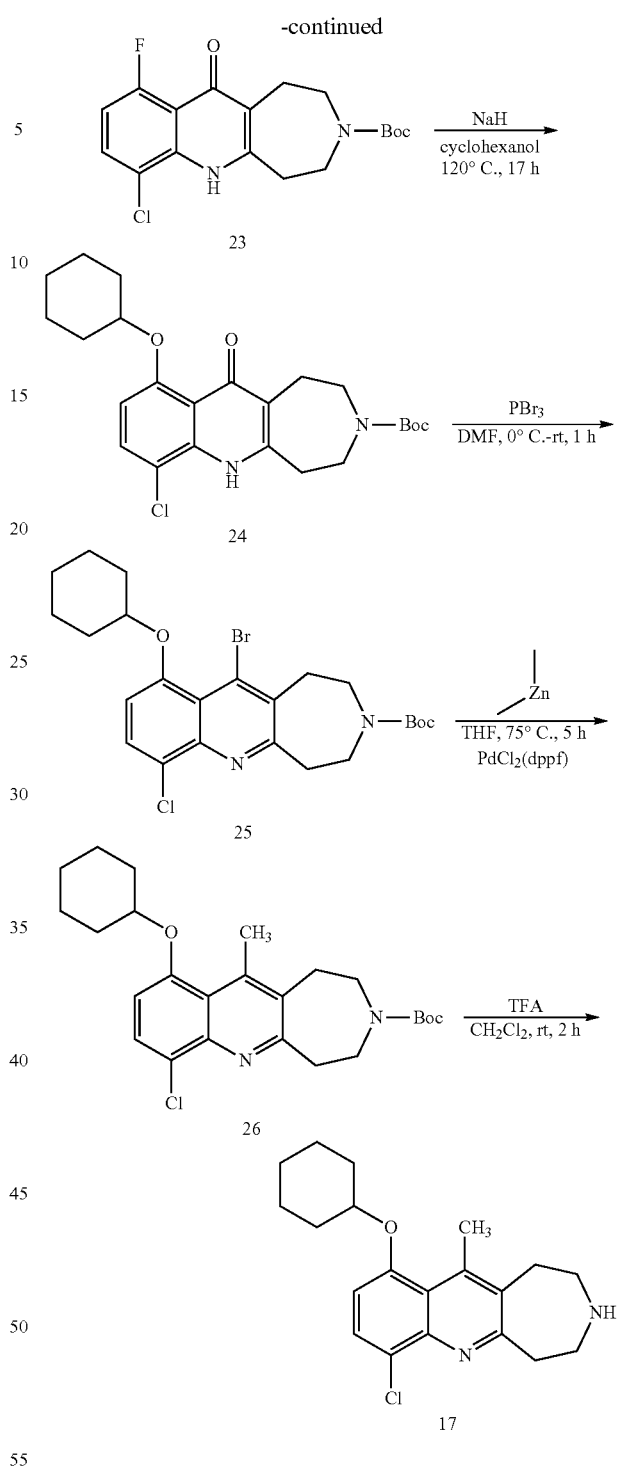

Step 1: 7-Chloro-10-fluoro-11-oxo-4,5,6,11-tetrahydro-1H-azepino[4,5-b]quinoline-3(2H)-carboxylic tert-butyl ester (23)

12 g Polyphosphoric acid was added to a solution of 2-chloro-5-fluoroaniline (22, 6 g, 41.2 mmol) and 1-tert-butyl 4-ethyl 5-oxoazepane-1,4-dicarboxylate (14.11 g, 49.5 mmol) in 1,4-dioxane (10 mL). The mixture was heated to 120° C. for 15 h. Ice-water was added and the mixture then adjusted to pH 9 by dropwise addition of saturated aqueous K₂CO₃. Di-tert-butyl dicarbonate (9.00 g, 41.2 mmol) was added to the mixture which was stirred for 5 h. The mixture was partitioned between EtOAc and brine. The organic layer was then dried over Na₂SO₄, filtered, and concentrated in vacuo. The resulting crude product was recrystallized from EtOAc and petroleum ether to give the title compound. ¹HNMR (400 MHz, CDCl₃): δ 8.11 (s, 1H), 7.55 (dd, J=4.4 Hz, 8.0 Hz, 1H), 6.88 (dd, J=8.8 Hz, 10.8 Hz, 1H), 4.98 (s, 1H), 3.74-3.72 (m, 2H), 3.54-3.52 (m, 2H), 3.02-2.98 (m, 4H), 1.48 (s, 9H); MS (ESI) m/z: calcd 367.81 (M+H), found 367.8.

Step 2: 7-Chloro-10-(cyclohexyloxy)-11-oxo-4,5,6, 11-tetrahydro-1H-azepino[4,5-b]quinoline-3(2H)-carboxylic acid tert-butyl ester (24)

Sodium hydride (1.963 g, 49.2 mmol, 60%) was added to cyclohexanol (24.6 g, 245.4 mmol). 7-Chloro-10-fluoro-11-oxo-4,5,6,11-tetrahydro-1H-azepino[4,5-b]quinoline-3 (2H)-carboxylic acid tert-butyl ester (23, 3 g, 8.18 mmol, from Step 1) was added to the reaction solution. The mixture was stirred for 17 h at 130° C. Water was then added dropwise to the mixture and the mixture was extracted with EtOAc. The organic solvent was removed by concentration in vacuo, and the crude product was recrystallized from EtOAc and petroleum ether to give the title compound. ¹HNMR (400 MHz, CDCl₃): δ 7.58 (d, J=8.4 Hz, 1H), 6.74 (d, J=8.4 Hz, 1H), 4.61-4.59 (m, 1H), 3.61-3.55 (m, 4H), 3.48-3.43 (m, 2H), 3.07-3.03 (m, 2H), 2.11-2.07 (m, 2H), 2.04-2.01 (m, 2H), 1.98-1.85 (m, 2H), 1.83-1.74 (m, 2H), 1.65-1.57 (m, 2H), 1.47 (s, 9H); MS (ESI) m/z: calcd 447.97 (M+H), found 447.9.

Step 3: 11-Bromo-7-chloro-10-(cyclohexyloxy)-2,3, 4,5-tetrahydro-1H-azepino[4,5-b]quinoline-3-carboxylic acid tert-butyl ester (25)

7-Chloro-10-(cyclohexyloxy)-11-oxo-4,5,6,11-tetrahydro-1H-azepino[4,5-b]quinoline-3(2H)-carboxylic acid tert-butyl ester (24, 1 g, 2.237 mmol, from Step 2) in DMF (15 mL) was treated dropwise with phosphorus tribromide (0.727 g, 2.68 mmol) over 10 min. After stirring and cooling to room temperature, ice-water was added and the mixture was stirred for 30 min and then adjusted to pH 8 by dropwise addition of 50% aqueous NaOH with cooling. The mixture was extracted with EtOAc. The organic layer was dried with Na₂SO₄, filtered, and concentrated in vacuo. The resulting crude product was purified by flash chromatography (silica gel, eluting with 0% to 18% EtOAc in petroleum ether) to give the title compound.
¹HNMR (400 MHz, CDCl₃): δ 7.64 (d, J=8.4 Hz, 1H), 6.88 (d, J=8.4 Hz, 1H), 4.47-4.43 (m, 1H), 3.70-3.65 (m, 4H), 3.48-3.45 (m, 2H), 3.41-3.39 (m, 2H), 2.10-2.08 (m, 2H), 1.88-1.86 (m, 2H), 1.73-1.71 (m, 2H), 1.62-1.59 (m, 2H), 1.46 (s, 9H), 1.39-1.37 (m, 2H); MS (ESI): calcd 510.86 (M+H), found 510.9.

Step 4: 7-Chloro-10-(cyclohexyloxy)-11-methyl-2,3, 4,5-tetrahydro-1H-azepino[4,5-b]quinoline-3-carboxylic acid ten-butyl ester (26)

11-Bromo-7-chloro-10-(cyclohexyloxy)-2,3,4,5-tetrahydro-1H-azepino[4,5-b]quinoline-3-carboxylic acid ten-butyl ester (2.5, 70 mg, 0.137 mmol, from Step 3) and PdCl₂(dppf) (5 mg) was dissolved in dry THF (5.0 ml) and 1M dimethylzinc (0.165 ml, 0.165 mmol) was added. The mixture was stirred for 4 h at 75° C. and then cooled to rt. Water (10 mL) was then added and the mixture was extracted with EtOAc (2×15 mL). The combined organic extracts were washed with brine, dried over MgSO₄, and concentrated in vacuo. The resulting crude product, was purified by column chromatography (silica, gel, eluting with 0% to 15% EtOAc in petroleum ether) to afford the title compound, ¹HNMR (400 MHz, CDCl₃): δ 7.58 (d, J=8.8 Hz, 1H), 6.76 (d, J=8.4 Hz, 1H), 4.43-4.41 (m, 1H), 3.69-3.63 (m, 4H), 3.38-3.34 (in, 2H), 3.13-3.09 (m, 2H), 2.88 (s, 3H), 2.09-2.04 (m, 2H), 1.83-1.79 (m, 2H), 1.66-1.61 (m, 4H), 1.48-1.44 (m, 2H), 1.46 (s, 9H); MS (ESI) m/z: calcd 445.99 (M+H), found 445.9.

Step 5: 7-Chloro-10-(cyclohexyloxy)-11-methyl-2,3, 4,5-tetrahydro-1H-azepino[4,5-b]quinoline (27)

7-Chloro-10-(cyclohexyloxy)-11-methyl-2,3,4,5-tetrahydro-1H-azepino[4,5-b]quinoline-3-carboxylic acid Serf-butyl ester (26, 25 mg, 0.056 mmol, from Step 4) was dissolved in 5:1 DCM/TFA. (5 mL) and the mixture was stirred at rt for 30 min. The TFA was removed under by concentration in vacuo and the resulting material was partitioned between EtOAc (5 mL) and 1M aqueous K₂CO₃ (2 mL). Additional solid K₂CO₃ was added to maintain a basic aqueous pH. The organic layer was separated, dried with Na₂SO₄, filtered, and concentrated in vacuo. The resulting residue was placed under vacuum overnight to give the title compound.

¹HNMR (400 MHz, CD₃OD): δ 7.72 (d, J=8.4 Hz, 1H), 7.05 (d, J=8.8 Hz, 1H), 4.60-4.56 (m, 1H), 3.61-3.58 (m, 2H), 3.46-3.41 (m, 6H), 2.98 (s, 3H), 2.11-2.09 (m, 2H), 1.83-1.82 (m, 2H), 1.71-1.66 (m, 3H), 1.63-1.49 (m, 3H); MS (ESI) m/z: calcd 345.88 (M+H), found 345.9.

EXAMPLE 4

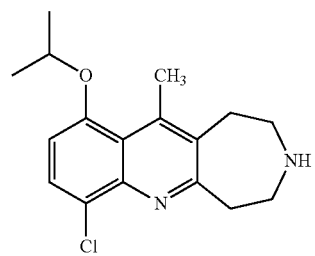 [SMILES: Cc1c2c(nc3c(Cl)ccc(OC(C)C)c13)CCNCC2]

7-Chloro-10-(isopropoxy)-11-methyl-2,3,4,5-tetrahydro-1H-azepino[4,5-b]quinoline

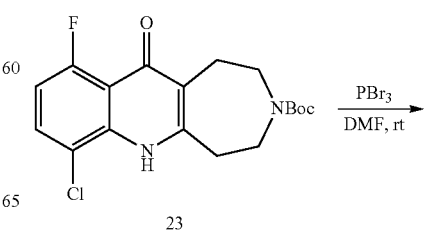

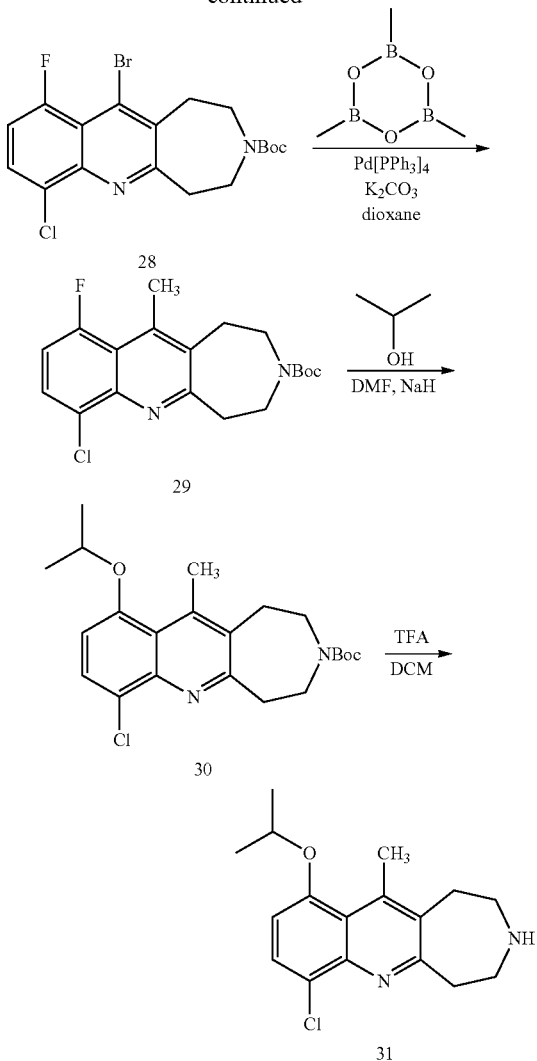

Step 1: 11-Bromo-7-chloro-10-fluoro-2,3,4,5-tetrahydro-1H-azepino[4,5-b]quinoline-3-carboxylic acid tert-butyl ester (28)

To a solution of 7-chloro-10-fluoro-11-oxo-4,5,6,11-tetrahydro-1H-azepino[4,5-b]quinoline-3(2H)-carboxylic tert-butyl ester (23, 300 mg, 0.818 mmol) in DMF (5.0 mL) was slowly added PBr$_3$ (332 mg, 1.227 mmol). The mixture was stirred for 0.5 h at it and solid K$_2$CO$_3$ was added to adjust the pH to 7-8. The mixture was then extracted with ethyl acetate (20 mL) and the organic layer was washed with saturated NaHCO$_3$, dried over Na$_2$SO$_4$, filtered and concentrated in vacuo to give the title compound as a white solid. MS (EST) m/z: calcd 429.09 (M+H); found 429.1.

Step 2: 7-Chloro-10-fluoro-11-methyl-1,2,4,5-tetrahydro-1H-azepino[4,5-b]quinoline-3-carboxylic acid ten-butyl ester (29)

To a solution of 11-bromo-7-chloro-10-fluoro-1,2,4,5-tetrahydro-1H-azepino[4,5-b]quinoline-3-carboxylic acid tert-butyl ester (28, 100 mg, 0.233 mmol, from Step 1) is 1,4-dioxane (2.5 mL) were added water (0.5 mL), 2,4,6-trimethyl-cyclotriboroxane (58 mg, 0.465 mmol), K$_3$PO$_4$ (148 mg, 0.698 mmol), and Pd(PPh$_3$)$_4$ (10 mg) The reaction mixture was stirred for 0.5 h at 100° C. with microwave irradiation After the starting material was consumed, water was added followed by extraction with ethyl acetate (3×10 mL). The combined organic extracts were dried over Na$_2$SO$_4$, filtered and concentrated in vacuo. The crude product was purified by column chromatography on silica gel eluting with 15:1 petroleum ether/ethyl acetate to give the title compound as a colorless solid. MS (ESI) m/z: calcd 365.14 (M+H); found 365.2.

Step 3: 7-Chloro-10-isopropoxy-11-methyl-1,2,4,5-tetrahydro-1H-azepino[4,5-b]quinoline-3-carboxylic acid tert-butyl ester (30)

A 10-mL microwave tube was charged with 7-chloro-10-fluoro-11-methyl-2,3,4,5-tetrahydro-1H-azepino[4,5-b]quinoline-3-carboxylic acid tert-butyl ester (29, 25 mg, 0.069 mmol, from Step 2), DMF (2.0 mL), isopropanol (12 mg, 0.206 mmol), and sodium hydride (5.0 mg, 0.125 mmol, 60%). The reaction mixture was stirred for 0.5 h at 120° C. under microwave irradiation. After the starting material was consumed, water was added to the reaction mixture followed by extraction with ethyl acetate. The organic layer was dried with Na$_2$SO$_4$, filtered and concentrated in vacuo. The residue was subjected to purification by flash chromatography (silica gel, petroleum ether:ethyl acetate=9:1) to give the title compound as a white solid. MS (ESI) m/z: calcd 405.19 (M+H); found 405.2.

Step 4: 7-Chloro-10-isopropoxy-11-methyl-2,3,4,5-tetrahydro-1H-azepino[4,5-b]quinoline (31)

To a solution of 7-chloro-10-isopropoxy-11-methyl-2,3,4,5-tetrahydro-1H-azepino[4,5-b]quinoline-3-carboxylic acid tert-butyl ester (30, 20 mg, 0.049 mmol, from Step 3) in DCM (2.0 mL) was added TFA (1.0 mL) and the mixture was stirred for 1.0 h at rt. The mixture solution was then concentrated in vacuo, and saturated aqueous NaHCO$_3$ solution was added to adjust the pH to 7-8. The mixture was extracted with ethyl acetate (3×10 mL), and the combined organic extracts were dried with Na$_2$SO$_4$, filtered and concentrated in vacuo to give the title compound as a white solid, MS (ESI) m/z: calcd 305.13 (M+H); found 305.2.

EXAMPLE 5

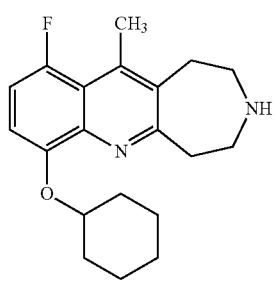 [SMILES: Cc1c2c(nc3c(OC4CCCCC4)ccc(F)c13)CCNCC2]

7-(Cyclohexyloxy)-10-fluoro-11-methyl-2,3,4,5-tetrahydro-1H-azepino[4,5-b]quinoline

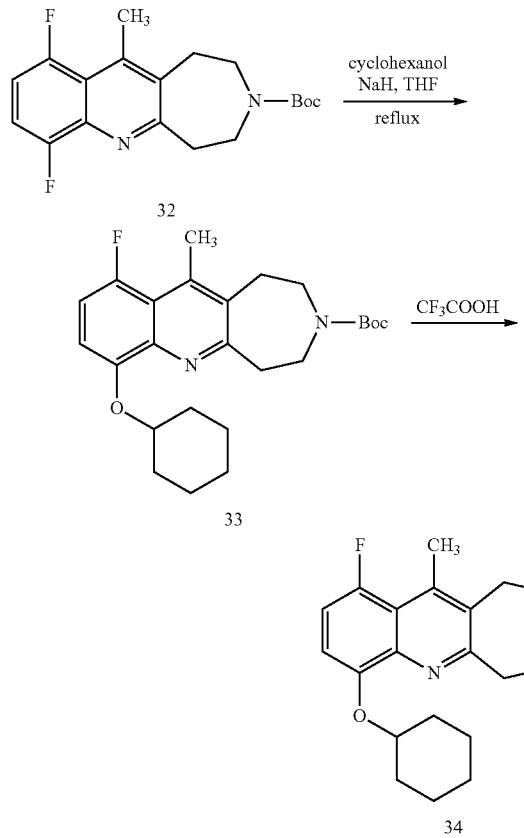

Step 1: 7-(Cyclohexyloxy)-10-fluoro-11-methyl-2,3,4,5-tetrahydro-1H-azepino[4,5-b]quinoline-3-carboxylic acid tert-butyl ester (33)

To a solution of cyclohexanol (100 mg) in THF (2.0 mL) was added sodium hydride (24 mg, 0.6 mmol) and the mixture was stirred for 10 rain at rt. 7,10-Difluoro-11-methyl-2,3,4,5-tetrahydro-1H-azepino[4,5-b]quinoline-3-carboxylic acid tert-butyl ester (32, 70 mg, 0.2 mmol, from Example 6, Step 3) was then added, and the reaction mixture was heated at reflux temperature overnight. The mixture was then cooled to rt and water added. The mixture was extracted with DCM, and the combined organic extracts were washed with brine, dried over anhydrous Na$_2$SO$_4$ and concentrated in vacuo to give the crude product which was purified by column chromatography on silica gel eluting with 0-10% EtOAc in petroleum ether to give the title compound. $^1$H NMR (400 MHz, CDCl$_3$): δ 7.04-6.99 (m, 2H), 4.39-4.34 (m, 1H), 3.67-3.63 (m, 4H), 3.35 (s, 2H), 3.11 (s, 2H), 2.77 (s, 3H), 2.13-2.11 (m, 2H), 1.87-1.85 (m, 2H), 1.69-1.59 (m, 4H), 1.46 (s, 9H), 1.35-1.33 (m, 2H). MS (ESI) m/z: calcd 429.2 (M+H); found 428.9.

Step 2: 7-(Cyclohexyloxy)-10-fluoro-11-methyl-2,3,4,5-tetrahydro-1H-azepino[4,5-b]quinoline (34)

To a solution of 7-(cyclohexyloxy)-10-fluoro-11-methyl-2,3,4,5-tetrahydro-1H-azepino[4,5-b]quinoline-3-carboxylic acid fen-butyl ester (33, 41.2 mg, 0.096 mmol, from Step 1) in DCM (2.0 mL) was added TFA (0.5 mL) and the solution was stirred at rt. After the starting material was consumed the mixture was concentrated in vacuo. The residue was dissolved in water, and the pH was adjusted to basic with NaHCO$_3$. The mixture was extracted with DCM. The organic extracts were washed with brine, dried over anhydrous Na$_2$SO$_4$, and concentrated in vacuo to give the title compound. $^1$H NMR (400 MHz, CDCl$_3$): δ 7.03-6.98 (m, 2H), 4.38-4.33 (m, 1H), 3.39-3.36 (m, 2H), 3.13-3.03 (m, 6H), 2.77 (s, 3H), 2.14-2.11 (m, 2H), 1.86-1.85 (m, 2H), 1.72-1.60 (m, 4H), 1.38-1.30 (m, 2H). MS (ESI) m/z: calcd 329.2 (M+H); found 329.1.

EXAMPLE 6

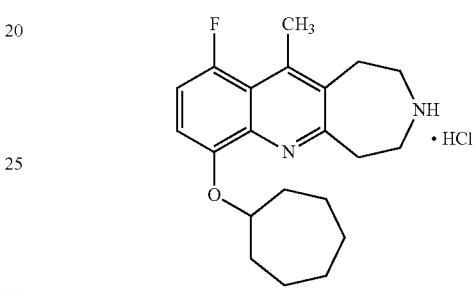

7-(Cycloheptyloxy)-10-fluoro-11-methyl-2,3,4,5-tetrahydro-1H-azepino[4,5-b]quinoline, hydrochloride

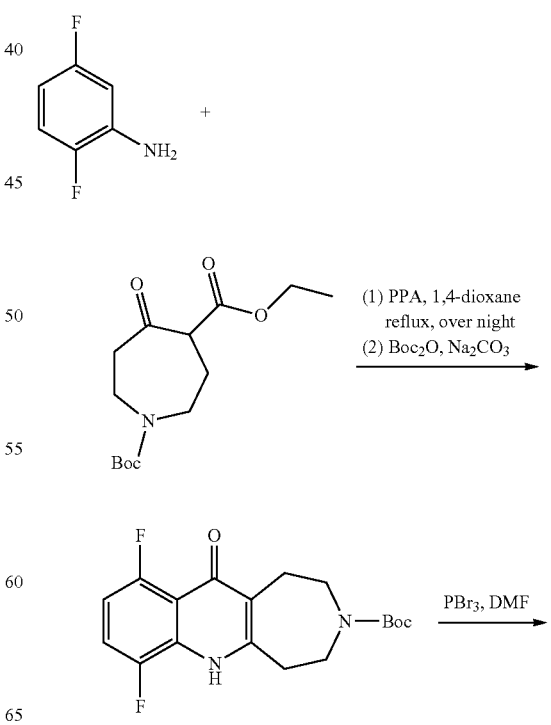

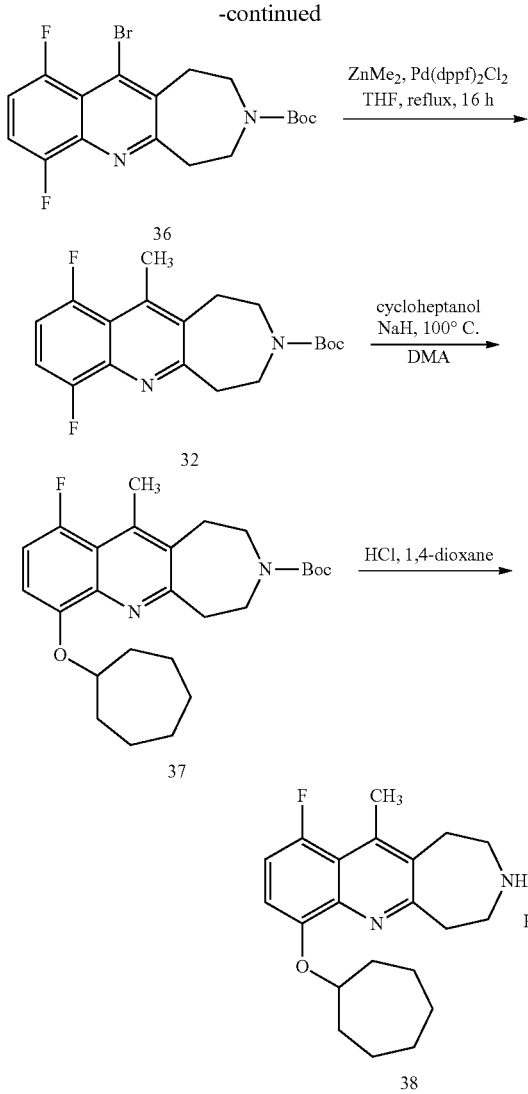

Step 1: 7,10-Difluoro-11-oxo-4,5,6,11-tetrahydro-1H-azepino[4,5-b]quinoline-3(2H)-carboxylic acid tert-butyl ester (35)

A mixture of 2,5-difluoroaniline (5.0 g, 38.8 mmol), 1-ten-butyl 4-ethyl 5-oxoazepane-1,4-dicarboxylate (13 g, 45.6 mmol) and polyphosphoric acid (10 g) in 1,4-dioxane (30 mL) was stirred overnight at reflux temperature. After the starting material was consumed, the mixture was poured into stirred water (20 mL) and solid potassium carbonate was added to adjust the pH to 8-10. Di-tert-butyl dicarbonate (10 g, 45.9 mmol) in ethanol (10 mL) was then added and the mixture was stirred at rt for 3 h. The mixture was then concentrated in vacuo and the residue was extracted with DCM. The organic extract was dried over anhydrous sodium sulfate, concentrated in vacuo and the resulting solid was recrystallized from ethyl acetate and petroleum ether to give the title compound as a white solid. $^1$H NMR (400 MHz, CDCl$_3$): δ 8.28 (bs, 1H), 7.25-7.15 (m, 1H), 6.85-6.78 (m, 1H), 3.75-3.68 (m, 2H), 3.60-3.48 (m, 2H), 3.10-2.90 (m, 4H), 1.48 (s, 9H), MS (ESI) m/z: calcd 351.14 (M+H), found 351.1.

Step 2: 11-Bromo-7,10-difluoro-2,3,4,5-tetrahydro-1H-azepino[4,5-b]quinoline-3-carboxylic acid tert-butyl ester (36)

To a solution of 7,10-difluoro-11-oxo-2,3,4,5-tetrahydro-1H-azepino[4,5-b]quinoline-3(2H)-carboxylic acid tert-butyl ester (35, 7.0 g, 20 mmol, from Step 1) in anhydrous DMF (30 mL) was added phosphorus tribromide (6.5 g, 24 mmol) at 0° C. The mixture was stirred at rt for 1.0 h. After the starting material was consumed, the reaction mixture was added to aqueous sodium carbonate solution (100 mL) dropwise with cooling in an ice bath. The product was extracted with ethyl acetate (100 mL), and the organic extract was washed with brine, dried over anhydrous sodium sulfate, and concentrated in vacuo to give the title compound as a light-yellow solid. $^1$H NMR (400 MHz, CDCl$_3$): δ 7.40-7.28 (m, 1H), 7.22-7.12 (m, 1H), 3.72-3.65 (m, 4H), 3.50-3.35 (m, 4H), 1.47 (s, 9H).

Step 3: 7,10-Difluoro-11-methyl-2,3,4,5-tetrahydro-1H-azepino[4,5-b]quinoline-3-carboxylic acid tert-butyl ester (32)

To a solution of 11-bromo-7,10-difluoro-2,3,4,5-tetrahydro-1H-azepino[4,5-b]quinoline-3-carboxylic acid tert-butyl ester (36, 4.1 g, 10 mmol, from Step 2) in anhydrous THF (40 mL) was added Pd(dppf)$_2$Cl$_2$ (0.3 g, 0.37 mmol) and dimethylzinc (20 mL, 1.0 M in toluene) at 0° C. The mixture was stirred at reflux temperature for 18 h. After the starting material was consumed, water (1.0 mL) was slowly added dropwise to the mixture at 0° C. The mixture was stirred for 15 min, then sodium sulfate was added and the mixture was stirred for an additional 15 min. The mixture was filtered and the filtrate was concentrated. The crude product was purified by column chromatography on silica gel eluting with 0-10% EtOAc in petroleum ether to give the title compound as a white solid.

Step 4: 7-(Cycloheptyloxy)-10-fluoro-11-methyl-2,3,4,5-tetrahydro-1H-azepino[4,5-b]quinoline-3-carboxylic acid tert-butyl ester (37)

To a solution of cycloheptanol (3.0 g, 26.3 mmol) in N,N-dimethylacetamide (DMA) (5.0 mL) was added sodium hydride (0.32 g, 8.0 mmol) and the mixture was stirred at rt for 0.5 h. tert-Butyl 7,10-difluoro-11-methyl-4,5-dihydro-1H-azepino[4,5-b]quinoline-3(2H)-carboxylate (32, 1.0 g, 2.87 mmol, from Step 3) was then added and the mixture was stirred at 100° C. for 1 h. After the starting material was consumed, the mixture was allowed to cool to rt, and water was added. The product was extracted with ethyl acetate. The organic extract was dried over anhydrous sodium sulfate, filtered, and concentrated in vacuo. The crude product was subjected to purification by column chromatography on silica gel eluting with 0-10% EtOAc in petroleum ether to give the title compound as a white solid. $^1$H NMR (400 MHz, CDCl$_3$): δ 7.03 (dd, J=8.4 Hz, J=13.2 Hz, 1H), 6.90 (dd, J=4.0 Hz, J=8.4 Hz, 1H), 4.55-4.50 (m, 1H), 5.05-5.00 (m, 1H), 3.68-3.62 (m, 4H), 3.37-3.34 (m, 2H), 3.15-3.10 (m, 2H), 2.76 (d, J=4.2 Hz, 3H), 2.18-2.12 (m, 2H), 2.02-1.90 (m, 2H), 1.82-1.75 (m, 2H), 1.70-1.55 (m, 4H), 1.55-1.40 (m, 11H); MS (ESI): calcd 443.26 (M+H), found 443.0.

Step 5: 7-(Cycloheptyloxy)-10-fluoro-11-methyl-2,3,4,5-tetrahydro-1H-azepino[4,5-b]quinoline, hydrochloride (38)

A solution of 7-(cycloheptyloxy)-10-fluoro-11-methyl-2,3,4,5-tetrahydro-1H-azepino[4,5-b]quinoline-3-carboxylic acid fen-butyl ester (37, 0.50 g, 1.13 mmol, from Step 4) in a hydrogen chloride/1,4-dioxane solution was stirred at rt for 1 h. After the starting material was consumed, the solvent was removed in vacuo to give the title compound as a yellow solid.

$^1$H NMR (400 MHz, CD$_3$OD): δ 7.61 (dd, J=8.8 Hz, J=12.8 Hz, 1H), 7.53 (dd, J=3.2 Hz, J=8.8 Hz, 1H), 4.11-4.00 (m, 2H), 3.70-3.55 (m, 4H), 3.55-3.45 (m, 2H), 3.10 (d, J=4.2 Hz, 3H), 2.30-2.16 (m, 2H), 2.08-1.95 (m, 2H), 1.90-1.78 (m, 2H), 1.75-1.52 (m, 6H). MS (ESI) m/z: calcd 343.21 (M+H), found 343.0.

EXAMPLE 7

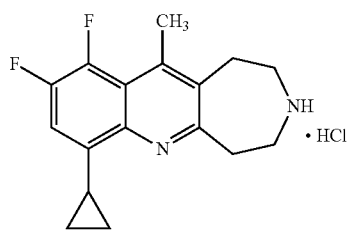 [SMILES: Cc1c2c(nc3c(C4CC4)cc(F)c(F)c13)CCNCC2 ; "· HCl"]

7-Cyclopropyl-9,10-difluoro-11-methyl-2,3,4,5-tetrahydro-1H-azepino[4,5-b]quinoline, hydrochloride

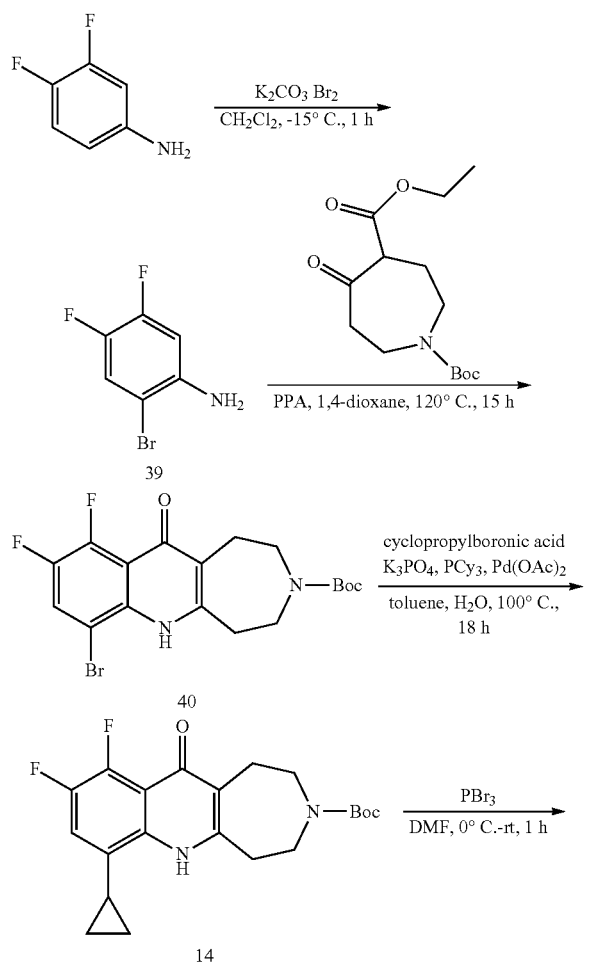

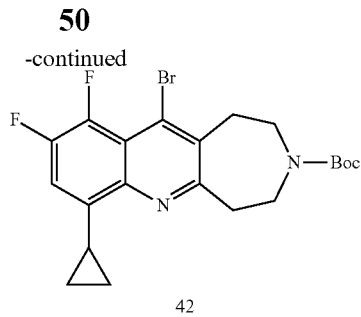

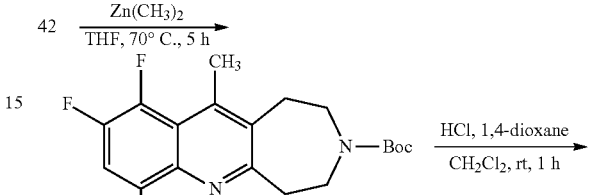

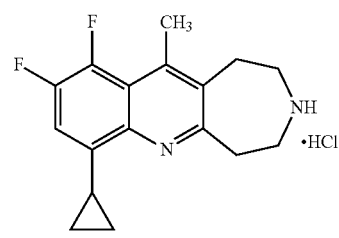

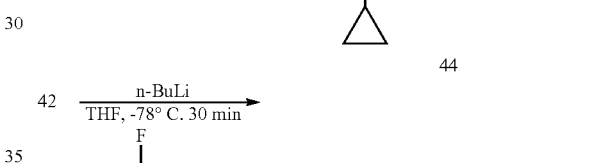

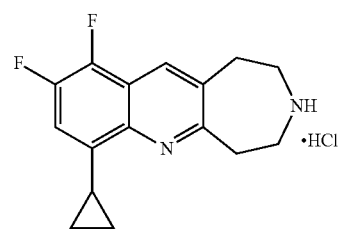

Step 1: 2-Bromo-4,5-difluoroaniline (39)

To a solution of bromine (30.9 g, 194 mmol) in CH$_2$Cl$_2$ (100 mL) was added dropwise into a suspension of 3,4-difluoroaniline (25 g, 194 mmol) and potassium carbonate (26.72 g, 194 mmol) in CH$_2$Cl$_2$ (800 mL) at −15° C. After the addition was completed, the mixture was stirred at the same temperature for 30 min. The reaction mixture was then poured into ice water and it was extracted with DCM. The organic extract was washed with brine, dried over anhydrous sodium sulfate and concentrated in vacuo to give the crude title product as the brown solid.

¹H NMR (400 MHz, CDCl₃): δ 7.24-7.22 (m, 1H), 6.60-6.55 (m, 1H), 3.99 (bs, 2H); MS (ESI) m/z: calcd 130.11 (M+H), found 130.1.

Step 2: tert-Butyl 7-bromo-9,10-difluoro-11-oxo-4,5,6,11-tetrahydro-1H-azepino[4,5-b]quinoline-3(2H)-carboxylate (40)

PPA (12 g) was added to a solution of 5-bromo-2-chloro-4-fluoroaniline (39, 6 g, 41.2 mmol, from Step 1) and 1-tert-butyl 4-ethyl 5-oxoazepane-1,4-dicarboxylate (14.11 g, 49.5 mmol) dissolved 1,4-dioxane (10 mL). The solution was heated to 120° C. for 15 h. Ice water was added, and the mixture was adjusted to pH=9 by dropwise addition of saturated aqueous $K_2CO_3$. Di-tert-butyl dicarbonate (9.00 g, 41.2 mmol) was then added to the solution which was stirred for 5 h, then the mixture was partitioned between DCM and saturated brine solution. The organic layer was then dried over $Na_2SO_4$, filtered, concentrated in vacuo and the crude product recrystallized from EtOAc and petroleum ether to give the title compound.
¹HNMR (400 MHz, CDCl₃): δ 8.06 (s, 1H), 7.695 (m, 1H), 3.74-3.72 (m, 2H), 3.53-3.51 (m, 2H), 3.01-2.96 (m, 4H), 1.48 (s, 9H); MS (ESI) m/z: calcd 430.25 (M+H), found 430.3.

Step 3: tert-Butyl 7-cyclopropyl-9,10-difluoro-11-oxo-4,5,6,11-tetrahydro-1H-azepino[4,5-b]quinoline-3(2H)-carboxylate (41)

To a solution of ten-butyl 7-bromo-9,10-difluoro-11-oxo-2,3,4,5-tetrahydro-1H-azepino[4,5-b]quinoline-3(2H)-carboxylate (40, 6.8 g, from Step 2), cyclopropylboronic acid (2.6 g, 31.6 mmol), $K_3PO_4$, $H_2O$ (14.6 g, 63.0 mmol) and tricyclohexylphosphine (0.88 g, 3.16 mmol) in toluene (50.0 mL) and water (3 mL) under a nitrogen atmosphere was added diacetoxypalladium (0.34 g, 1.6 mmol). The mixture was heated to 100° C. overnight and then cooled to room temperature. Water (100 mL) was added and the mixture was extracted with EtOAc. The combined organic extracts were washed with brine, dried over $MgSO_4$ and concentrated in vacuo to afford a crude residue which was purified by flash chromatography (silica gel, eluting with 0% to 20% EtOAc in petroleum ether) to give the title compound. MS (ESI) m/z: calcd. 391.42 (M+H), found 391.0.

Step 4: tert-Butyl 11-bromo-7-cyclopropyl-9,10-difluoro-4,5-dihydro-1H-azepino[4,5-b]quinoline-3(2H)-carboxylate (42)

tert-Butyl 7-cyclopropyl-9,10-difluoro-11-oxo-4,5,6,11-tetrahydro-1H-azepino

[4,5-b]quinoline-3(2H)-carboxylate (41, 4.8 g, 12.3 mmol, from Step 3) in DMF (25 mL) was treated dropwise with tribromophosphine (10.0 g, 37 mmol) over 10 min. The mixture was stirred at rt for 1 h. After the starting material was consumed, ice water was added and the mixture was stirred for 30 min. The mixture was then adjusted to pH=8 by dropwise addition of 50% NaOH with cooling. The mixture was extracted with ethyl acetate. The organic extract was then dried with $Na_2SO_4$, filtered, and concentrated in vacuo and the resulting material was purified by flash chromatography (silica gel, eluting with 0% to 10% EtOAc in petroleum ether) to give the title compound.
¹HNMR (400 MHz, CDCl₃): δ 6.92 (m, 1H), 3.70-3.65 (m, 4H), 3.48-3.45 (m, 2H), 3.41-3.39 (m, 2H), 3.23-3.19 (m, 1H), 1.46 (s, 9H), 1.31-1.29 (m, 2H), 0.78-0.76 (m, 2H); MS (ESI) m/z: calcd 454.32 (M+H), found 454.0.

Step 5: tert-Butyl 7-cyclopropyl-9,10-difluoro-11-methyl-4,5-dihydro-1H-azepino[4,5-b]quinoline-3(2H)-carboxylate (43)

tert-Butyl 11-bromo-7-cyclopropyl-9,10-difluoro-2,3,4,5-tetrahydro-1H-azepino

[4,5-b]quinoline-3(2H)-carboxylate (4:2, 2.2 g, 4.83 mmol, from Step 4) and $PdCl_2$ (dbbf) (80 mg) were dissolved in THF (5.0 mL), Dimethylzinc (0.922 g, 9.66 mmol) was added and the mixture was stirred for 4 h at 70° C. and then cooled to room temperature. Water (10 mL) was added and the mixture was extracted with EtOAc (2×15 mL). The combined organic extracts were washed with brine, dried over $MgSO_4$ and concentrated in vacuo. The resulting material was purified by flash chromatography on silica gel eluting with 0% to 10% EtOAc in petroleum ether to afford the title compound.
¹HNMR (400 MHz, CDCl₃): δ 6.85 (dd, J=8.4, 11.2, 1H), 3.70-3.64 (m, 4H), 3.32-3.30 (m, 2H), 3.27-3.25 (m, 1H), 3.13-3.10 (m, 2H), 2.78 (s, 3H), 1.45 (s, 9H), 1.15-1.13 (m, 2H), 0.78-0.76 (m, 2H); MS (ESI) m/z: calcd 389.35 (M+H), found 389.0.

Step 6: 7-Cyclopropyl-9,10-difluoro-11-methyl-2,3,4,5-tetrahydro-1H-azepino[4,5-b]quinoline, hydrochloride (44)

tert-Butyl 7-cyclopropyl-9,10-difluoro-11-methyl-4,5-dihydro-1H-azepino[4,5-b]quinoline-3(2H)-carboxylate (43, 1.5 g, 3.86 mmol, from Step 5) was dissolved in $CH_2Cl_2$ (10 mL) and HQ (gas) in 1,4-dioxane (5 mL) was added. The mixture was stirred at ambient temperature until all the starting material was consumed and then concentrated in vacuo. The resulting product was dried under vacuum overnight to give the title compound.
¹HMMR (400 MHz, CD₃OD): δ 7.24 (dd, J=8.8, 11.6, 1H), 3.70-3.64 (m, 4H), 3.32-3.30 (m, 2H), 3.27-3.25 (m, 1H), 3.13-3.10 (m, 2H), 2.78 (s, 3H), 1.15-1.13 (m, 2H), 0.78-0.76 (m, 2H); MS (ESI) m/z: calcd 289.35, (M+H) found 289.0.

Alternative synthesis of 7-cyclopropyl-9,10-difluoro-2,3,4,5-tetrahydro-1H-azepino[4,5-b]quinoline (Example 2), as the hydrochloride Salt (21b)

Step 1: tert-Butyl 7-cyclopropyl-9,10-difluoro-4,5-dihydro-1H-azepino[4,5-b]quinoline-3(2H)-carboxylate (20)

11-Bromo-7-cyclopropyl-9,10-difluoro-4,5,6,11-tetrahydro-1H-azepino[4,5-b]quinoline 3(2H)-carboxylate (42, 2.2 g, 4.83 mmol, from Step 4) was suspended in THF (50 mL), and the mixture was cooled to −78° C. After the addition of n-BuLi (3.8 mL of 2.5 mol/L in THF, 9.6 mmol), the yellow solution was stirred at −78° C. for 60 min. The reaction mixture was quenched by the addition of saturated aqueous ammonium chloride solution (15 mL). The layers were separated and the aqueous phase was extracted with EtOAc, the organic phase was dried over anhydrous $Na_2SO_4$, concentrated, and the residue was purified by flash chromatography on silica gel eluting with 0% to 10% EtOAc in petroleum ether to afford the title compound.

¹HNMR (400 MHz, CDCl₃): δ 8.07 (s, 1H), 6.83 (t, J=8.2 Hz, 1H), 3.70-3.67 (m, 4H), 3.36-3.34 (m, 2H), 3.24-3.22 (m, 1H), 3.09-3.05 (m, 2H), 1.55 (s, 9H), 1.27-1.24 (m, 2H), 0.82-0.80 (m, 2H); MS (ESI) m/z: calcd. 375.42 (M+H), found 375.4.

Step 2: 7-Cyclopropyl-9,10-difluoro-2,3,4,5-tetrahydro-1H-azepino[4,5-b]quinoline, hydrochloride (21b)

tert-Butyl 7-cyclopropyl-9,10-difluoro-4,5-dihydro-1H-azepino[4,5-b]quinoline-3(2)-carboxylate (20, 1.5 g, 3.86 mmol, from Step 2) was dissolved in dissolved in CH₂Cl₂ (10 mL) and HCl (gas) in 1,4-dioxane (5 mL) was added. The mixture was stirred at ambient temperature for 1 h and then concentrated in vacuo. The resulting product was dried under vacuum overnight to give the title compound.

¹HNMR (400 MHz, CD₃OD): δ 8.31 (s, 1H), 7.10 (t, J=8.8 Hz, 1H), 3.58-3.55 (m, 2H), 3.49-3.43 (m, 4H), 3.39-3.34 (m, 2H), 3.20-3.18 (m, 1H), 1.16-1.13 (m, 2H), 0.85-0.83 (m, 2H); MS (ESI) m/z: calcd. 275.42 (M+H), found 275.4.

The following additional Examples shown in the Table below were prepared following the procedures outlined in Methods and detailed in Examples 1-7.

| Example | Structure | MS Data (ESI, Q⁺) |
|---|---|---|
| 8 | 10-chloro-7-cyclopropyl-2,3,4,5-tetrahydro-1H-azepino[4,5-b]quinoline | MS (ESI) m/z: (M + H) calcd 273.12; found, 273.1 |
| 9 | 7-cyclopropyl-8,10-difluoro-11-methyl-2,3,4,5-tetrahydro-1H-azepino[4,5-b]quinoline | MS (ESI) m/z (M + H) calcd 289.15; found, 289.0 |
| 10 | 7-cyclopropyl-8,10-difluoro-2,3,4,5-tetrahydro-1H-azepino[4,5-b]quinoline | MS (ESI) m/z (M + H) calcd 275.14; found, 275.1 |
| 11 | 10-chloro-7-cyclopropyl-9-fluoro-2,3,4,5-tetrahydro-1H-azepino[4,5-b]quinoline | MS (ESI) m/z: (M + H) calcd 291.11; found, 291.1 |
| 12 | 7-chloro-10-(4-fluorophenoxy)-2,3,4,5-tetrahydro-1H-azepino[4,5-b]quinoline | MS (ESI) m/z: (M + H) calcd 343.10; found, 343.1 |
| 13 | 10-chloro-7-cyclopropyl-11-methyl-2,3,4,5-tetrahydro-1H-azepino[4,5-b]quinoline | MS (ESI) m/z: (M + H) calcd 287.13; found, 287.0 |
| 14 | 7-cyclohexyloxy-10-fluoro-2,3,4,5-tetrahydro-1H-azepino[4,5-b]quinoline | MS (ESI) m/z: (M + H) calcd 315.19; found, 315.2 |

-continued

| Example | Structure | MS Data (ESI, Q+) |
|---|---|---|
| 15 | 7-chloro-10-cyclohexyloxy-2,3,4,5-tetrahydro-1H-azepino[4,5-b]quinoline | MS (ESI) m/z: (M + H) calcd 331.16; found, 331.1 |
| 16 | 7-chloro-10-cycloheptyloxy-11-methyl-2,3,4,5-tetrahydro-1H-azepino[4,5-b]quinoline | MS (ESI) m/z: (M + H) calcd 359.19; found, 359.2 |

EXAMPLES OF PHARMACEUTICAL FORMULATIONS

As a specific embodiment of an oral composition of a compound of the present invention, 50 mg of the compound of any of the Examples 1-16 is formulated with sufficient, finely divided lactose to provide a total amount of 580 to 590 mg to fill a size O hard gelatin capsule.

As a second specific embodiment of an oral pharmaceutical composition, a 100 mg potency tablet, is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:
1. A compound of structural formula I:

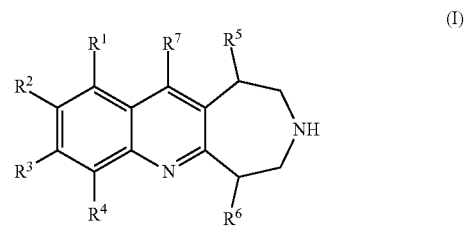

or a pharmaceutically acceptable salt thereof; wherein
$R^1$ is selected from the group consisting of:
  hydrogen,
  halogen,
  $C_{2-6}$ alkyl, optionally substituted with one to five substituents independently selected from fluorine and hydroxy,
  $(CH_2)_m$—$C_{3-7}$ cycloalkyl,
  $C_{2-6}$ alkoxy, optionally substituted with one to five substituents independently selected from fluorine and hydroxy,
  $C_{3-7}$ cycloalkyloxy,
  $C_{1-6}$ alkylthio, optionally substituted with one to five substituents independently selected from fluorine and hydroxy,
  $C_{1-6}$ alkylsulfonyl, optionally substituted with one to five substituents independently selected from fluorine and hydroxy,
  —O(CH$_2$)$_n$-aryl, and
  —O(CH$_2$)$_n$-heteroaryl;
wherein cycloalkyl and cycloalkyloxy are optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy, wherein alkyl and alkoxy are optionally substituted with one to five fluorines; wherein aryl and heteroaryl are optionally substituted with 1 to 5 groups independently selected from halogen, hydroxyl, cyano, $CO_2H$, $C_{1-4}$ alkyloxycarbonyl, $C_{1-4}$ alkyl, and $C_{1-4}$ alkoxy, wherein alkyl and alkoxy are optionally substituted with one to five fluorines; and $(CH_2)_m$ or $(CH_2)_n$ is optionally substituted with 1 to 2 substituents independently selected from fluorine, hydroxyl, methyl, trifluoromethyl, and methoxy, or wherein two substituents when on the same methylene ($CH_2$) group are taken together with the carbon atom to which they are attached to form a cyclopropyl group;
$R^2$ is selected from the group consisting of:
  hydrogen,
  halogen,
  $C_{1-4}$ alkyl, and
  $C_{3-6}$ cycloalkyl;
$R^3$ is hydrogen or halogen;
$R^4$ is selected from the group consisting of:
  halogen,
  $C_{2-6}$ alkyl, optionally substituted with one to five substituents independently selected from fluorine and hydroxy,
  $C_{3-7}$ cycloalkyl, $C_{2-6}$ alkoxy, optionally substituted with one to five substituents independently selected from fluorine and hydroxy, and $C_{3-7}$ cycloalkyloxy;

wherein cycloalkyl and cycloalkyloxy are optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy, wherein alkyl and alkoxy are optionally substituted with one to five fluorines;

$R^5$ and $R^6$ are each independently hydrogen or methyl;

$R^7$ is selected from the group consisting of:
hydrogen,
halogen,
$C_{1-3}$ alkyl, optionally substituted with one to five substituents independently selected from fluorine and hydroxy,
$C_{1-3}$ alkoxy, optionally substituted with one to five substituents independently selected from fluorine and hydroxy,
$C_{1-3}$ alkylthio, optionally substituted with one to five substituents independently selected from fluorine and hydroxy,
$C_{1-3}$ alkylsulfonyl, optionally substituted with one to five substituents independently selected from fluorine and hydroxyl,
amino,
$C_{1-4}$ alkylamino, and
di-($C_{1-4}$ alkyl)amino;

m is an integer from 0 to 1; and n is an integer from 0 to 2;

with the proviso that when $R^1$ is hydrogen or halogen and $R^2$ is hydrogen, halogen or methyl, then $R^4$ cannot be halogen.

2. The compound of claim 1 wherein $R^1$ is halogen; $R^2$ is hydrogen or halogen; $R^3$ is hydrogen or halogen; $R^4$ is optionally substituted $C_{3-6}$ cycloalkyl; $R^5$ and $R^6$ are both hydrogen; and $R^7$ is hydrogen or methyl; wherein cycloalkyl is optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

3. The compound of claim 2 wherein $R^4$ is cyclopropyl.

4. The compound of claim 2 wherein $R^1$ is fluorine or chlorine; $R^2$ is hydrogen, fluorine, or chlorine; $R^3$ is hydrogen or fluorine; $R^4$ is $C_{3-6}$ cycloalkyl; and $R^7$ is hydrogen or methyl; wherein cycloalkyl is optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

5. The compound of claim 4 wherein $R^4$ is cyclopropyl.

6. The compound of claim 1 wherein $R^1$ is halogen; $R^2$ is hydrogen or halogen; $R^3$ is hydrogen or halogen; $R^4$ is optionally substituted $C_{3-6}$ cycloalkyloxy; $R^5$ and $R^6$ are both hydrogen; and $R^7$ is hydrogen or methyl; wherein cycloalkyloxy is optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

7. The compound of claim 6 wherein $R^4$ is cyclohexyloxy or cycloheptyloxy optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

8. The compound of claim 6 wherein $R^1$ is fluorine or chlorine; $R^2$ is hydrogen, fluorine, or chlorine; $R^3$ is hydrogen or fluorine; $R^4$ is optionally substituted $C_{3-6}$ cycloalkyloxy; and $R^7$ is hydrogen or methyl; wherein cycloalkyloxy is optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

9. The compound of claim 8 wherein $R^4$ is cyclohexyloxy or cycloheptyloxy optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

10. The compound of claim 1 wherein $R^1$ is selected from the group consisting of:
$C_{5-7}$ cycloalkyloxy, optionally substituted optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy; and phenoxy, optionally substituted with 1 to 3 groups independently selected from halogen, hydroxyl, cyano, $C_{1-4}$ alkyloxycarbonyl, $C_{1-4}$ alkyl, and $C_{1-4}$ alkoxy;

$R^2$ and $R^3$ are each hydrogen or halogen;

$R^4$ is halogen;

$R^5$ and $R^6$ are both hydrogen; and $R^7$ is hydrogen or methyl.

11. The compound of claim 10 wherein $R^2$ is hydrogen, fluorine, or chlorine; $R^3$ is hydrogen or fluorine; $R^4$ is chlorine or fluorine; and $R^7$ is hydrogen or methyl.

12. The compound of claim 11 wherein $R^1$ is cyclohexyloxy or cycloheptyloxy optionally substituted with 1 to 3 groups independently selected from halogen, hydroxyl, cyano, $CO_2H$, $C_{1-4}$ alkyloxycarbonyl, $C_{1-4}$ alkyl, and $C_{1-4}$ alkoxy.

13. The compound of claim 11 wherein $R^1$ is phenoxy optionally substituted with 1 to 3 groups independently selected from halogen, hydroxyl, cyano, $C_{1-4}$ alkyloxycarbonyl, $C_{1-4}$ alkyl, and $C_{1-4}$ alkoxy.

14. A compound selected from the group consisting of:
10-chloro-7-cyclopropyl-2,3,4,5-tetrahydro-1H-azepino[4,5-b]quinoline;
7-cyclopropyl-8,10-difluoro-11-methyl-2,3,4,5-tetrahydro-1H-azepino[4,5-b]quinoline;
7-ethyl-10-fluoro-2,3,4,5-tetrahydro-1H-azepino[4,5-b]quinoline;
7-ethyl-2,3,4,5-tetrahydro-1H-azepino[4,5-b]quinoline;
7-cyclopropyl-10-fluoro-2,3,4,5-tetrahydro-1H-azepino[4,5-b]quinoline;
7-chloro-10-ethyl-9-fluoro-2,3,4,5-tetrahydro-1H-azepino[4,5-b]quinoline;
7-chloro-10-ethyl-2,3,4,5-tetrahydro-1H-azepino[4,5-b]quinoline;
7-cyclopropyl-8,10-difluoro-2,3,4,5-tetrahydro-1H-azepino[4,5-b]quinoline;
10-ethyl-7,9-difluoro-2,3,4,5-tetrahydro-1H-azepino[4,5-b]quinoline;
7-chloro-10-cyclohexyloxy-11-methyl-2,3,4,5-tetrahydro-1H-azepino[4,5-b]quinoline;
7-cyclopropyl-8,10-difluoro-2,3,4,5-tetrahydro-1H-azepino[4,5-b]quinoline;
7-isopropyl-2,3,4,5-tetrahydro-1H-azepino[4,5-b]quinoline;
10-ethyl-7-fluoro-2,3,4,5-tetrahydro-1H-azepino[4,5-b]quinoline;
10-chloro-7-ethyl-2,3,4,5-tetrahydro-1H-azepino[4,5-b]quinoline;
7-cyclopropyl-9,10-difluoro-2,3,4,5-tetrahydro-1H-azepino[4,5-b]quinoline;
7-cyclopropyl-9,10-difluoro-11-methyl-2,3,4,5-tetrahydro-1H-azepino[4,5-b]quinoline;
10-chloro-7-cyclopropyl-9-fluoro-2,3,4,5-tetrahydro-1H-azepino[4,5-b]quinoline;
7-fluoro-10-isopropyl-2,3,4,5-tetrahydro-1H-azepino[4,5-b]quinoline;

7-chloro-10-(3-fluorophenoxy)-2,3,4,5-tetrahydro-1H-azepino[4,5-b]quinoline;
7-cycloheptyloxy-10-fluoro-11-methyl-2,3,4,5-tetrahydro-1H-azepino[4,5-b]quinoline;
7-cyclohexyloxy-10-fluoro-11-methyl-2,3,4,5-tetrahydro-1H-azepino[4,5-b]quinoline;
7-cyclopropyl-10-ethyl-9-fluoro-2,3,4,5-tetrahydro-1H-azepino[4,5-b]quinoline;
10-chloro-7-cyclopropyl-11-methyl-2,3,4,5-tetrahydro-1H-azepino[4,5-b]quinoline;
10-cyclopropyl-7-fluoro-2,3,4,5-tetrahydro-1H-azepino[4,5-b]quinoline;
7-chloro-10-phenoxy-2,3,4,5-tetrahydro-1H-azepino[4,5-b]quinoline;
7-cyclopropyl-9-fluoro-10-methyl-2,3,4,5-tetrahydro-1H-azepino[4,5-b]quinoline;
7-cyclohexyloxy-10-fluoro-2,3,4,5-tetrahydro-1H-azepino[4,5-b]quinoline;
7-chloro-10-isopropoxy-11-methyl-2,3,4,5-tetrahydro-1H-azepino[4,5-b]quinoline;
7-chloro-10-cyclohexyloxy-2,3,4,5-tetrahydro-1H-azepino[4,5-b]quinoline;
7-chloro-10-cyclopentyloxy-9-fluoro-2,3,4,5-tetrahydro-1H-azepino[4,5-b]quinoline;
7-chloro-10-cyclopentyloxy-2,3,4,5-tetrahydro-1H-azepino[4,5-b]quinoline;
7-chloro-10-cycloheptyloxy-11-methyl-2,3,4,5-tetrahydro-1H-azepino[4,5-b]quinoline;
7-chloro-9-cyclopropyl-2,3,4,5-tetrahydro-1H-azepino[4,5-b]quinoline;
7-chloro-10-cycloheptyloxy-2,3,4,5-tetrahydro-1H-azepino[4,5-b]quinoline;
7-chloro-10-cyclohexyloxy-11-ethyl-2,3,4,5-tetrahydro-1H-azepino[4,5-b]quinoline;
7-chloro-10-(3-fluorophenoxy)-2,3,4,5-tetrahydro-1H-azepino[4,5-b]quinoline;
10-benzyloxy-7-chloro-2,3,4,5-tetrahydro-1H-azepino[4,5-b]quinoline;
10-cyclopentyloxy-7-ethyl-9-fluoro-2,3,4,5-tetrahydro-1H-azepino[4,5-b]quinoline;
10-cyclopentyloxy-7-cyclopropyl-2,3,4,5-tetrahydro-1H-azepino[4,5-b]quinoline;
7-chloro-10-(2-fluorophenoxy)-11-methyl-2,3,4,5-tetrahydro-1H-azepino[4,5-b]quinoline;
10-cyclohexyloxy-7-fluoro-2,3,4,5-tetrahydro-1H-azepino[4,5-b]quinoline;
10-chloro-9-methoxy-7-cyclopropyl-2,3,4,5-tetrahydro-1H-azepino[4,5-b]quinoline;
7-chloro-10-cyclohexyloxy-11-dimethylamino-2,3,4,5-tetrahydro-1H-azepino[4,5-b]quinoline;
7-chloro-10-cyclobutyloxy-2,3,4,5-tetrahydro-1H-azepino[4,5-b]quinoline;
7,9-diisopropyl-2,3,4,5-tetrahydro-1H-azepino[4,5-b]quinoline; and
10-cyclopentyloxy-7-ethyl-2,3,4,5-tetrahydro-1H-azepino[4,5-b]quinoline;
or a pharmaceutically acceptable salt thereof.

15. The compound of claim 14 selected from the group consisting of:
10-chloro-7-cyclopropyl-2,3,4,5-tetrahydro-1H-azepino[4,5-b]quinoline;
7-cyclopropyl-8,10-difluoro-11-methyl-2,3,4,5-tetrahydro-1H-azepino[4,5-b]quinoline;
7-cyclopropyl-8,10-difluoro-2,3,4,5-tetrahydro-1H-azepino[4,5-b]quinoline;
7-chloro-10-cyclohexyloxy-11-methyl-2,3,4,5-tetrahydro-1H-azepino[4,5-b]quinoline;
7-cyclopropyl-9,10-difluoro-2,3,4,5-tetrahydro-1H-azepino[4,5-b]quinoline;
7-cyclopropyl-9,10-difluoro-11-methyl-2,3,4,5-tetrahydro-1H-azepino[4,5-b]quinoline;
10-chloro-7-cyclopropyl-9-fluoro-2,3,4,5-tetrahydro-1H-azepino[4,5-b]quinoline;
7-chloro-10-(3-fluorophenoxy)-2,3,4,5-tetrahydro-1H-azepino[4,5-b]quinoline;
7-cycloheptyloxy-10-fluoro-11-methyl-2,3,4,5-tetrahydro-1H-azepino[4,5-b]quinoline;
7-cyclohexyloxy-10-fluoro-11-methyl-2,3,4,5-tetrahydro-1H-azepino[4,5-b]quinoline;
10-chloro-7-cyclopropyl-11-methyl-2,3,4,5-tetrahydro-1H-azepino[4,5-b]quinoline;
7-cyclohexyloxy-10-fluoro-2,3,4,5-tetrahydro-1H-azepino[4,5-b]quinoline;
7-chloro-10-isopropoxy-11-methyl-2,3,4,5-tetrahydro-1H-azepino[4,5-b]quinoline;
7-chloro-10-cyclohexyloxy-2,3,4,5-tetrahydro-1H-azepino[4,5-b]quinoline; and
7-chloro-10-cycloheptyloxy-11-methyl-2,3,4,5-tetrahydro-1H-azepino[4,5-b]quinoline;
or a pharmaceutically acceptable salt thereof.

16. A pharmaceutical composition comprising a compound in accordance with claim 1 in combination with a pharmaceutically acceptable carrier.

17. A pharmaceutical composition comprising a compound in accordance with claim 14 in combination with a pharmaceutically acceptable carrier.

18. A method for treating obesity and obesity-related conditions selected from the group consisting of Type 2 diabetes, insulin resistance, dyslipidemia, atherosclerosis, and Metabolic Syndrome in a mammal in need thereof which comprises the administration to the mammal of a therapeutically effective amount of a compound of claim 1.

19. A method for treating schizophrenia, depression, psychosis, urinary incontinence, and tobacco smoking in a mammal in need thereof which comprises the administration to the mammal of a therapeutically effective amount of a compound of claim 1.

* * * * *